US009771603B2

(12) United States Patent
Smart et al.

(10) Patent No.: US 9,771,603 B2
(45) Date of Patent: Sep. 26, 2017

(54) FERMENTATION PROCESS

(71) Applicant: LanzaTech New Zealand Limited, Skokie, IL (US)

(72) Inventors: Kathleen Frances Smart, Chicago, IL (US); Alexander Paul Mueller, Chicago, IL (US); Michael James Harry Mawdsley, Skokie, IL (US); Christophe Daniel Mihalcea, Skokie, IL (US)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 291 days.

(21) Appl. No.: 14/493,287

(22) Filed: Sep. 22, 2014

(65) Prior Publication Data

US 2015/0087037 A1    Mar. 26, 2015

Related U.S. Application Data

(60) Provisional application No. 61/880,970, filed on Sep. 22, 2013.

(51) Int. Cl.
C12P 7/18    (2006.01)

(52) U.S. Cl.
CPC ......... *C12P 7/18* (2013.01); *C12Y 202/01006* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy | |
| 5,807,722 A | 9/1998 | Gaddy | |
| 5,821,111 A | 10/1998 | Grady et al. | |
| 6,136,577 A | 10/2000 | Gaddy | |
| 6,340,581 B1 | 1/2002 | Gaddy | |
| 6,368,819 B1 | 4/2002 | Gaddy et al. | |
| 6,753,170 B2 | 6/2004 | Gaddy et al. | |
| 8,143,037 B2 | 3/2012 | Zahn et al. | |

FOREIGN PATENT DOCUMENTS

| | | |
|---|---|---|
| EP | 117309 A1 | 9/1984 |
| WO | WO98/00558 A1 | 1/1998 |
| WO | WO00/68407 A1 | 11/2000 |
| WO | WO02/08438 A2 | 1/2002 |
| WO | WO2007/117157 A1 | 10/2007 |
| WO | WO2008/028055 A2 | 3/2008 |
| WO | WO2008/115080 A1 | 9/2008 |
| WO | WO2009/022925 A1 | 2/2009 |
| WO | WO2009/064200 A2 | 5/2009 |
| WO | WO2012/131627 A1 | 10/2012 |
| WO | 2013076144 A2 | 5/2013 |

OTHER PUBLICATIONS

PCT Search Report (PCT/US2014/056846) dated Dec. 29, 2014.
Abrini, J. Naveau, H. & Nyns, E. J., Archives of Microbiology, (1994), 161, 345-351.
Hensirisak et al., Scale-up of microbubble dispersion generator for aerobic fermentation, Applied Biochemistry and Biotechnology, Oct. 2002, vol. 101, No. 3.
Klasson K. T. et al., Bioconversion of synthesis gas into liquid or gaseous fuels, Enzyme and Microbial Technology, (1992), 14, 602-608.
Klasson K. T. et al., Bioreactors for synthesis gas fermentations resources, Conservation and Recycling, (1991), 5, 145-165.
Klasson, K. T. et al., Bioreactor design for synthesis gas fermentations, Fuel, (1991), 70, 605-614.
Liou et al., International Journal of Systematic and Evolutionary Microbiology, (2005), 33, pp. 2085-2091.
Perez, J. M. Richter, H. Loftus, S. E., & Angenent, L. T., Biocatalytic reduction of short chain carboxylic acids, Biotechnology and Bioengineering, (2012), 1-30.
Qin, Jiayang et al., Production of 2,3-Butanediol by Klebsiella Pneumoniae Using Glucose and Ammonium Phosphate, Chinese J. Chem. Eng., (2006), 14(1) 132-136.
Sakai et al., Biotechnology Letters, (2004), 29, pp. 1607-1612.
Svetlichny, V.A. Sokolova T.G. et al., Systematic and Applied Microbiology, (1991), 14, 254-260.
Syu MJ, Biological production of 2,3 butanediol, Appl Microbiol Biotechnol, (2001), 55:10-18.
Tirado-Acevedo O., Production of Bioethanol from Synthesis Gas Using Clostridium Ijungdahlii. PhD thesis, North Carolina State University, 2010.
Vega, J. L. et al., Design of Bioreactors for Coal Synthesis Gas Fermentations, Resources, Conservation and Recycling, (1990), 3. 149-160.
Vega, J. L. et al., Study of Gaseous Substrate Fermentation: Carbon Monoxide Conversion to Acetate. 2. Continuous Culture. Biotech. Bioeng., (1989), 34. 6. 785-793.
Vega, J. L., et al., Study of gaseous substrate fermentations: Carbon monoxide conversion to acetate. 1. Batch culture, Biotechnology and Bioengineering, (1989), 34. 6. 774-784.
Arfin et al., Purification and Properties of the Acetohydroxy Acid Isomeroreductase of *Salmonella typhimurium*. The Journal of Biomedical Chemistry, 1969, vol. 244, No. 5, pp. 1118-1127.
Aulabaugh et al., Oxalyl Hydroxamates as Reaction-Intermediate Analogues for Ketol-Acid Reductoisomerase, Biochemistry 1990, 29, pp. 2824-2830.

*Primary Examiner* — Paul Holland
(74) *Attorney, Agent, or Firm* — Frank S Molinaro

(57) ABSTRACT

A methods for altering the metabolite profile of a fermentation, by increasing flux through acetolactate. The methods comprises increasing production of one or more products derived from acetolactate. Further provided is a method for increasing the production of 2,3-butandiol by microbial fermentation of gaseous substrates, the method comprising providing a compound which inhibits one or more enzymes which convert acetolactate to branched chain amino acids to the fermentation. The present invention further provides methods for increasing the production of 2,3-butandiol relative to other fermentation products such as ethanol and acetic acid.

13 Claims, 7 Drawing Sheets

| | Carbon distribution in metabolites | | | | |
|---|---|---|---|---|---|
| | 2,3-BDO | Ethanol | Acetic acid | Biomass | Lactic acid |
| Before HIBA addition | 22.1% | 47.9% | 18.5% | 11.2% | 0.2% |
| After HIBA addition | 41.99% | 33.15% | 14.94% | 9.87% | 0.0% |

SEQUENCE LISTING

```
<160> NUMBER OF SEQ ID NOS: 2

<210> SEQ ID NO 1
<211> LENGTH: 996
<212> TYPE: DNA
<213> ORGANISM: Clostridium autoethanogenum
<220> FEATURE:
<221> NAME/KEY: misc_feature
<223> OTHER INFORMATION: Ketol-acid reductoisomerase gene

<400> SEQUENCE: 1
atgagtagta ttgaaaaggt ttatcatgat gaagatgtta atatggatgc acttaaaggt      60
aaggttgtag caataatggg atatggaagt cagggaagag gacaatccaa ttgcctaaga     120
gacaatggag taaatgttat aattggtgca ggaaataagg atagatatcc ggattgggaa     180
aatgcggaaa aagatggatt tactgtatat ccttttgatg aggcagttaa aaaagctgat     240
gtagtaatga tattacttca agaccctgct caacctgcag tttattatga atcaattcat     300
caaaatttaa gaccaaatca gacactttgc tttgcacatg ggtttgcaat attgtatgga     360
acaattgtgc caccagaatt tgtagatgta gtacttttg ttcctaatgg accaggtcct     420
gttgtaaggc aaaaatttct agatggttca ggaatatatg gtgcagttgc tgtagaccag     480
gatgttactg gacatgctaa agaaacagct cttgcgattg ctaaaggtgt tggcagcaca     540
agaactggta cagtatatat ttcattccaa catgagactg aaggagataa ctttgaagaa     600
caggttcttt atggtggaac aatcaatctt atgagggcag tgtatgaaac tatggctaag     660
aatggatatc caaaatcctt tgcttatgca aaggctataa ggtccattag gtcagtaatt     720
gacgatatag atcgagttgg aatagaagaa tatttgtcga aaagatgcag cagaacttgt     780
gaatttgcag ttagaacttc tggacccaga gttattaatt atgatgaaat tgaaaaaata     840
tttagagaaa ctgaaaaagg tgaatttgca aaaagatggt tattggaatt ccaatgcggt     900
atgcctactt taaacagatt gagaagaact cataagaatt cgaatatgga agttgtagga     960
aaagagtgga gagaaaagtt cagtaaagaa gtataa                                996

<210> SEQ ID NO 2
<211> LENGTH: 1671
<212> TYPE: DNA
<213> ORGANISM: Clostridium autoethanogenum
<220> FEATURE:
<221> NAME/KEY: misc_feature
<223> OTHER INFORMATION: Catabolic acetolactate synthase gene

<400> SEQUENCE: 2
atgaatagag atataaaaaa agaagtccaa ctaaatacag ctcaaatgct agtaaaatgt      60
```

```
ttagaagccg aaggagtaaa gtacatcttt ggtattcctg gtgaagaaaa cctagaaata    120
atgaatgcaa tttcagattc aactattgaa tttatcacaa cccgtcatga gcaaggtgct    180
gcatttatgg ccgacgttta tggacgttta acaggaaaag caggtgtttg cctatcaaca    240
ctaggaccag gtgccactaa cttagtaact ggtgtagcag atgctgatag tgatggtgct    300
ccggttgttg ctattacagg tcaagtaggt actgaaagaa tgcatataac atcgcaccaa    360
tttttagacc tttgcaaaat gttcgaacca atcacaaaga gaagtaaaca aatcgttcgt    420
cctgatactg taagtgagat tataagactt gttttttaagt atgctgaaag tgaaaagcct    480
ggagcatgcc acattgattt acctgtaaat attgcaaaaa tgcccgtagg tgctttagaa    540 aagccttttgg aaaagaagat tccaccaaag gaacatgcag atttatcaac aattgaggaa    600
gctgcaagtg aaatcttcaa agcaaaaaat cctattatct tagctggaag cggtgctata    660
agaggaaatt cttcaaaagc tgttacggaa tttgcaacta aattgaaaat tccagtaatt    720
aatacgatga tggcaaaagg tattattcca atggataaca agtattcaat gtggacaata    780
ggtattccac aaaaagatta tgtaaataaa attattgaag aggctgattt agtaattaca    840
attggatatg atattgtaga atatgcccca tccaaatgga atataaatgg ggacattaaa    900
attgtgcata tcgatgcaag accatcacac atcaataaac tttatcagcc catagtagaa    960
gtagttggtg atatttcaga tgctctatac aatatattga gaagaacttc tagcaaagat   1020
gaaccagtaa aagctttgga aattaaatca gaaatgctag ctgaacatga aagctatgca   1080
aatgacaatg cttttccaat gaaacccccaa agaatttttaa atgatgttag aaaggtcatg   1140
ggaccacatg acattgtcat atcagatgta ggtgcccata aaatgtggat tgccagacat   1200
tataactgct atgagcccaa tacatgtatt atttcaaacg gttttgctac aatgggtatt   1260
ggtgttccag gtgcaattgc agccaaatta attaatccag ataaaaaagt attggctatt   1320
gttggtgatg gcggtttcat gatgaataat caagaattag aaacagccct acgtattaaa   1380
actccaattg tagtttttaat atttaatgac agtaactacg gttaataaaa gtggaaacaa   1440
gaagaacact atggtaaaag ctgttatgta gattttacta atccagactt tgtaaagctt   1500
gcagaaagta tgtatgcaaa aggatatcga gtagaaaaag cagaagattt aattccaact   1560
ttagaagaag ctttcaaaca aaatgtacct gcagttattg attgtcaagt tgactatggt   1620
gaaaatataa agcttacaaa gcatttaaaa gaagtttatg aaaatatgta a             1671
```

FERMENTATION PROCESS

CROSS REFERENCE TO A RELATED APPLICATION

This application claims priority from Provisional Application No. 61/880,970 filed Sep. 22, 2013, the contents of which are hereby incorporated by reference.

FIELD

The present invention relates methods for altering the metabolite profile of a fermentation system using a compound. In particular the invention relates to methods for increasing production of products derived from acetolactate.

BACKGROUND OF THE INVENTION

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources. Alcohols suitable for use as biofuels include ethanol, butanol and 2,3-butanediol.

Ethanol is rapidly becoming a major hydrogen-rich liquid transport fuel around the world. Worldwide consumption of ethanol in 2002 was an estimated 10.8 billion gallons. The global market for the fuel ethanol industry is also predicted to grow sharply in future, due to an increased interest in ethanol in Europe, Japan, the USA and several developing nations.

Butanediols including 1,2-butanediol, 1,3-butanediol, 1,4-butanediol and 2,3-butanediol may be considered to have a variety of advantages over ethanol. Like ethanol, butanediols may be used directly as an automotive fuel additive. They may also be relatively easily transformed into a number of other potentially higher value and/or higher energy products. For example, 2,3-butanediol may be readily converted in a two step process into an eight-carbon dimer which can be used as aviation fuel.

2,3-butanediol derives its versatility from its di-functional backbone, i.e., 2 hydroxyl groups are located at vicinal C-atoms allowing the molecule to be transformed quite easily into substances such as butadiene, butadione, acetoin, methylethyl ketone etc. These chemical compounds are used as base molecules to manufacture a vast range of industrially produced chemicals.

In addition, 2,3-butanediol may be used as a fuel in an internal combustion engine. It is in several ways more similar to gasoline than it is to ethanol. As the interest in the production and application of environmentally sustainable fuels has strengthened, interest in biological processes to produce 2,3-butanediol (often referred to as bio-butanol) has increased.

Carbon Monoxide (CO) is a major by-product of the incomplete combustion of organic materials such as coal or oil and oil derived products. Although the complete combustion of carbon containing precursors yields CO2 and water as the only end products, some industrial processes need elevated temperatures favouring the build up of carbon monoxide over CO2. One example is the steel industry, where high temperatures are needed to generate desired steel qualities. For example, the steel industry in Australia is reported to produce and release into the atmosphere over 500,000 tonnes of CO annually.

Furthermore, CO is also a major component of syngas, where varying amounts of CO and H2 are generated by gasification of a carbon-containing fuel. For example, syngas may be produced by cracking the organic biomass of waste woods and timber to generate precursors for the production of fuels and more complex chemicals.

The release of CO into the atmosphere may have significant environmental impact. In addition, emissions taxes may be required to be paid, increasing costs to industrial plants. Since CO is a reactive energy rich molecule, it can be used as a precursor compound for the production of a variety of chemicals. However, this valuable feedstock has not been utilised to produce 2,3-butanediol.

It has been demonstrated that 2,3-butanediol can be produced by microbial fermentation of carbohydrate containing feedstock (Syu M J, Appl Microbiol Biotechnol 55:10-18 (2001), Qin et al., Chinese J Chem Eng 14(1):132-136 (2006)). 2,3-butanediol may also be produced by microbial fermentation of biomass from crops such as sugar beet, corn, wheat and sugarcane. However, the cost of these carbohydrate feed stocks is influenced by their value as human food or animal feed and the cultivation of starch or sucrose-producing crops for 2,3-butanediol production is not economically sustainable in all geographies. Therefore, it is of interest to develop technologies to convert lower cost and/or more abundant carbon resources into 2,3-butanediol.

Production of 2,3-butanediol by microbial fermentation of gaseous substrates comprising CO has been demonstrated. However, the production of 2,3-butanediol by these processes has been a secondary product. Production of other products including ethanol is favoured in fermentation. Butanediol has greater value than the other products produced in such fermentations. It is desirable to be able to affect the fermentation in such a way that the production of 2,3-butanediol is increased. It has previously been shown that increased 2,3-butandiol productivity was influenced by a rate of hydrogen consumption by a microbial culture (WO2012131627).

There remains a need on the art to increase the ability to produce valuable products from industrial gaseous substrates in economically beneficial ways. There is a need to enhance the production of 2,3-butanediol relative to the production of other products that are routinely produced in the fermentation of gaseous substrates by carboxydotrophic bacteria.

SUMMARY OF THE INVENTION

The present invention provides a response to the need in the art. The present invention provides methods for altering the metabolite profile of a fermentation. In particular, the invention provides methods for increasing flux through acetolactate. In certain embodiments the invention provides methods for increasing production of one or more products derived from acetolactate. In a particular embodiment the invention provides a method for increasing the production of 2,3-butandiol by microbial fermentation of gaseous substrates. The present invention further provides methods for increasing the production of 2,3-butandiol relative to other fermentation products such as ethanol and acetic acid.

In a first aspect, the invention provides a method of increasing the production of at least one product derived from acetolactate. The method comprises providing a gaseous substrate to a bioreactor containing a culture of one more carboxydotrophic acetogenic microorganisms in a liquid nutrient medium, to product at least one fermentation product.

In one embodiment the method comprises adding at least one compound to the liquid nutrient medium. In one embodiment the at least one compound impacts the metabolite profile of the fermentation. In one embodiment the addition of the at least one compound to the liquid nutrient medium inhibits the flux of carbon to branched chain amino acids.

In one embodiment the compound is a compound which inhibits one or more enzymes which convert acetolactate to branched chain amino acids. In one embodiment, the compound comprises a carboxylic acid moiety.

In one embodiment the compound is selected from the group consisting of compounds that are structurally related to 2-hydroxyisobutyric acid (2-HIBA), acetolactate, 2-oxo-3-hydroxyisovalerate and 2,3-hydroxy-3-methylbutanoate. In one embodiment the at least one compound is selected from the group consisting of 2-hydroxyisobutyric acid (2-HIBA), 2-hydroxyl-2-methylbutyric acid, 2-hydroxybutyrate, 2-hydroxy-3-methylbutyric acid, 2-keto-3-hydroxyisovalerate and 2-ketoisovalerate.

In one embodiment the at least one fermentation product is selected from the group consisting of acetic acid, ethanol, 2,3-butanediol, 2-butanone, 2-butanol, acetoin, iso-propanol, lactate, succinate, methyl ethyl ketone (MEK), propanediol, 2-propanol, acetoin, iso-butanol, citramalate, butadiene, poly lactic acid, isobutylene, 3-hydroxy propionate (3HP), acetone and fatty acids.

In one embodiment the at least one product derived from acetolactate is selected from the group consisting of 2,3-butanediol, 2-butanone, 2-butanol and acetoin.

In one embodiment, the production rate of the at least one product derived from acetolactate is increased by at least 10%, or at least 20%, or at least 30%, or at least 40%, or at least 50%, or at least 60%, or at least 70%, or at least 80%, or at least 90%, or at least 100%, or at least 110%, or at least 120%, or at least 130%, or at least 140%, or at least 150%.

In a second aspect, the invention provides a method of increasing the production of 2,3-butanediol. In one embodiment the method comprises providing a gaseous substrate to a bioreactor containing a culture of one or more carboxydotrophic acetogenic microorganisms in a liquid nutrient medium to produce 2,3-butanediol. In one embodiment the fermentation produces at least one other fermentation product.

In one embodiment the method further comprises providing at least one compound to the liquid nutrient medium. In one embodiment, the at least one compound inhibits the flux of carbon to branched chain amino acids.

In one embodiment the compound is a compound which inhibits one or more enzymes which convert acetolactate to branched chain amino acids. In one embodiment, the compound comprises a carboxylic acid moiety.

In one embodiment the compound is selected from the group consisting of compounds that are structurally related to 2-hydroxyisobutyric acid (2-HIBA), acetolactate, 2-oxo-3-hydroxyisovalerate and 2,3-hydroxy-3-methylbutanoate. In one embodiment the at least one compound is selected from the group consisting of 2-hydroxyisobutyric acid (2-HIBA), 2-hydroxyl-2-methylbutyric acid, 2-hydroxybutyrate, 2-hydroxy-3-methylbutyric acid, 2-keto-3-hydroxyisovalerate and 2-ketoisovalerate.

In one embodiment the at least one other fermentation products Is selected from the group consisting of acetic acid, ethanol, 2-butanone, 2-butanol, acetoin, iso-propanol, lactate, succinate, methyl ethyl ketone (MEK), propanediol, 2-propanol, acetoin, iso-butanol, citramalate, butadiene, poly lactic acid, isobutylene, 3-hydroxy propionate (3HP), acetone and fatty acids.

In one embodiment at least one other fermentation products is at least ethanol. In one embodiment, the addition of the compound causes a shift in the metabolite profile of the fermentation. In one embodiment the addition the compound to the fermentation increases the production of 2,3-butanediol.

In one embodiment, the production rate of 2,3-butaenediol is increased by at least 10%, or at least 20%, or at least 30%, or at least 40%, or at least 50%, or at least 60%, or at least 70%, or at least 80%, or at least 90%, or at least 100%, or at least 110%, or at least 120%, or at least 130%, or at least 140%, or at least 150%

In embodiments of the first and second aspect, the gaseous substrate is selected from the group consisting of CO, CO2, H2, N2, CH4 and mixtures thereof. In particular embodiment, the gaseous substrate comprises at least CO.

In a third aspect, the invention provides a method of increasing the production of 2,3-butanediol. In one embodiment the method comprises providing a gaseous substrate to a bioreactor containing a culture of one or more carboxydotrophic acetogenic microorganisms in a liquid nutrient medium to produce at least 2,3-butanediol and ethanol, and manipulating the culture using one or more means to increase the rate of production of 2,3-butandiol.

In one embodiment, the step of manipulating the culture includes the addition of one or more compounds to the fermentation. In one embodiment, the compound is a compound which inhibits one or more enzymes which convert acetolactate to branched chain amino acids. In one embodiment, the compound comprises a carboxylic acid moiety. In one embodiment the one or more compounds is selected from the group consisting of compounds that are structurally related to 2-HIBA, acetolactate, 2-oxo-3-hydroxyisovalerate and 2,3-dihydroxy-3-methylbutanoate. In one embodiment, the one or more chemical compounds are selected from the group consisting of 2-HIBA, 2-hydroxyl-2-methylbutyric acid, 2-hydroxybutyrate, 2-hydroxy-3-methylbutyric acid, 2-keto-3-hydroxyisovalerate and 2-ketoisovalerate.

In one embodiment, the gaseous substrate further comprises at least one substrate selected from the group consisting of CO2, H2, N2, CH4 and mixtures thereof.

In one embodiment, the method of manipulating the culture comprises adding 2-HIBA to the culture. In one embodiment, one or more further manipulating steps are carried out in conjunction with adding 2-HIBA to the microbial culture. In one embodiment, the addition of 2-HIBA to the fermentation is controlled such that the concentration of 2_HIBA in the fermentation broth is maintained at a predetermined level. In certain embodiments the concentration of 2-HIBA is maintained at between 0.01 to 2.0 g/L (0.096 mM to 19.2 mM). In one embodiment the concentration of 2-HIBA is maintained at between 0.05 mM and 50 mM.

In one embodiment the addition of 2-HIBA to the fermentation, increases the production of 2,3-butandiol. In one embodiment, the addition of 2-HIBA improves the ratio of ethanol to 2,3-butandiol in favour of 2,3-butanediol. In particular embodiments the ratio of ethanol to 2,3-BDO is 4:1, of 3:1, or 2:1, or 1:1, or 1:2

In one embodiment, the production rate of 2,3-butaenediol is increased by at least 10%, or at least 20%, or at least 30%, or at least 40%, or at least 50%, or at least 60%, or at least 70%, or at least 80%, or at least 90%, or at least 100%, or at least 110%, or at least 120%, or at least 130%, or at least 140%, or at least 150%.

In particular embodiments, the microorganism is capable of utilising CO to produce 2,3-BDO at a concentration of 10 g/L or more. In particular embodiments, the microorganism is capable of utilising CO to produce 2,3-BDO at a concentration of greater than 12 g/L, or greater than 16 g/L, or greater than 20 g/L. In one embodiment the microorganism is capable of producing 2,3-butanediol at a rate of at least 10 g/L/day, or at least 15 g/L/day, or at least 20 g/L/day, or at least 25 g/L/day.

In particular embodiments, the microorganism is capable of utilising CO to produce ethanol at a concentration of 10 g/L or more. In particular embodiments, the microorganism is capable of utilising CO to produce ethanol at a concentration of greater than 15 g/L, or greater than 20 g/L, or greater than 30 g/L, or greater than 40 g/L.

In one embodiment, the fermentation further produces acetic acid. In particular embodiments, the microorganism is capable of utilising CO to produce acetic acid at a concentration below 10 g/L or less.

In embodiments of the first to third aspects, the one or more carboxydotrophic acetogenic microorganism is selected from the group consisting of *Clostridium, Moorella, Oxobacter, Peptostreptococcus, Acetobacterium, Eubacterium*, or *Butyribacterium*. In various embodiments, the microorganism is selected from the group comprising *Clostridium autoethanogenum, Clostridium ljungdahli, Clostridium carboxidivorans, Clostridium drakei, Clostridium scatologenes, Clostridium aceticum, Clostridium formicoaceticum, Clostridium magnum, Butyribacterium methylotrphoicum, Acetobacterium woodii, Alkalibaculum bacchi, Blautia producta, Eubacterium limosum, Moorella thermoacetica, Sporomusa ovata, Sporomusa silvacetica, Sporomusa sphaeroides, Oxobacter pfennigii* and *Thermoanaerobacter kiuvi*.

In particular embodiments, the microorganism is *Clostridium autoethanogenum* or *Clostridium ljungdahlii*. In one particular embodiment, the microorganism is *Clostridium autoethanogenum*. In a particular embodiment, the microorganim has the identifying characteristics of accession number DSMZ10061 or DSMZ23693.

In a fourth aspect, the invention provides a method for increasing the production of at least one product derived from acetolactate, the method comprising providing a gaseous substrate to a bioreactor comprising a culture of at least one recombinant acetogenic carboxydotrophic microorganism in a liquid nutrient medium, to produce at least one fermentation product; wherein the at least one recombinant microorganism has at least one genetic modification to increase the conversion of pyruvate to acetolactate.

In one embodiment the at least one genetic modification is selected from the group consisting of an inactivating mutation in a gene for a ketol-acid-reductoisomerase, and a modification which is adapted to provide overexpression of an acetolactate synthase gene.

In one embodiment, the recombinant microorganism has both a modification to provide over expression of an acetolactate synthase compared to a parental microorganisms; and an inactivating mutation in a gene for ketol-acid-reductoisomerase, in which activity of the ketol-acid-reductoisomerase is reduced compared to the parental microorganism.

In one embodiment the at least one genetic modification, results in an increase in production of acetolactate. In one embodiment, the reduction in activity of a ketol-acid-reductoisomerase, inhibits the production of branched chain amino acids. In one embodiment, an increased activity of an acetolactate synthase gene increases the rate of conversion of pyruvate to acetolacte.

In a fifth aspect, the invention provides a carboxydotrophic acetogenic microorganism which comprises an inactivating mutation in a gene for a ketol-acid-reductoisomerase.

In one embodiment, the carboxydotrophic acetogenic microorganism has a reduced ability to convert acetolactate to branched chain amino acids compared to a parental microorganism, upon growth and/or fermentation of a gaseous substrate.

In one embodiment, the carboxydotrophic microorganism further comprises one or more genetic modifications adapted to provide overexpression of an acetolactate synthase gene.

In a sixth aspect, the invention provides a carboxydotrophic acetogenic microorganism which comprises one or more genetic modification which is adapted to increase the level of activity of an acetolactate synthase.

In one embodiment, the one or more genetic modification which is adapted to increase the level of acetolactate synthase is selected from the group consisting of the overexpression of an endogenous catabolic acetolactate synthase, the overexpression of an endogenous anabolic acetolactate synthase, the substitution of an endogenous acetolactate synthase with an exogenous catabolic acetolactate synthase, the substitution of an endogenous acetolactate synthase with an exogenous anabolic acetolactate synthase, and the overexpression of a subunit of an endogenous anabolic synthase, said subunit being insensitive to feedback inhibition by branched chain amino acids In one embodiment the microorganism has a higher production rate of acetolactate compared to a parental microorganism, and/or produces a higher amount of an acetolactate derived product compared to a parental microorganism, upon growth and/or fermentation of a gaseous substrate.

In particular embodiments of the fourth to sixth aspects, the parental microorganism is a carboxydotrophic microorganism. In various embodiments, the carboxydotrophic microorganism is selected from *Clostridium, Moorella, Oxobacter, Peptostreptococcus, Acetobacterium, Eubacterium*, or *Butyribacterium*. In various embodiments, the microorganism is selected from the group comprising *Clostridium autoethanogenum, Clostridium ljungdahli, Clostridium carboxidivorans, Clostridium drakei, Clostridium scatologenes, Clostridium aceticum, Clostridium formicoaceticum, Clostridium magnum, Butyribacterium methylotrphoicum, Acetobacterium woodii, Alkalibaculum bacchi, Blautia producta, Eubacterium limosum, Moorella thermoacetica, Sporomusa ovata, Sporomusa silvacetica, Sporomusa sphaeroides, Oxobacter pfennigii* and *Thermoanaerobacter kiuvi*.

In particular embodiments, the parental microorganism is *Clostridium autoethanogenum* or *Clostridium ljungdahlii*. In one particular embodiment, the parental microorganism is *Clostridium autoethanogenum*. In a particular embodiment, the parental microorganism has the identifying characteristics of accession number DSMZ10061 or DSMZ23693.

In one embodiment the gas substrate is selected from the group consisting of CO, CO2, H2, N2, CH4 and mixtures thereof.

In one embodiment, the amount of an acetolactate derived product produced by a method of this aspect of the invention compared to a method performed using a parental microorganism is at least about 10% higher, at least about 20% higher, at least about 30% higher, at least about 40% higher, at least about 50% higher, at least about 60% higher, at least about 70% higher, at least about 80% higher, at least about 90% higher, at least about 100% higher, at least about 110% higher, at least about 120% higher, at least about 130% higher, at least about 140% higher, at least about 150% higher. In one embodiment, the amount of an acetolactate derived product produced by a method of this aspect of the invention is about 98% higher.

In particular embodiments, the recombinant carboxydotrophic acetogenic microorganism is capable of utilising CO to produce 2,3-BDO at a concentration of 10 g/L or more. In particular embodiments, the microorganism is capable of utilising CO to produce 2,3-BDO at a concentration of greater than 12 g/L, or greater than 16 g/L, or greater than 20 g/L. In one embodiment the microorganism is capable of producing 2,3-butanediol at a rate of at least 10 g/L/day, or at least 15 g/L/day, or at least 20 g/L/day, or at least 25 g/L/day.

In particular embodiments, the recombinant carboxydotrophic acetogenic microorganism is capable of utilising CO to produce ethanol at a concentration of 10 g/L or more. In particular embodiments, the microorganism is capable of utilising CO to produce ethanol at a concentration of greater than 15 g/L, or greater than 20 g/L, or greater than 30 g/L, or greater than 40 g/L. In particular embodiments, the microorganism is capable of utilising CO2 and H2 to produce acetic acid at a concentration below 10 g/L or less In particular embodiments the recombinant carboxydotrophic acetogenic microorganism produces ethanol and 2,3-butanediol at a ratio of ethanol to 2,3-BDO of 4:1, of 3:1, or 2:1, or 1:1, or 1:2.

The invention also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DETAILED DESCRIPTION OF THE INVENTION

Figure 1:
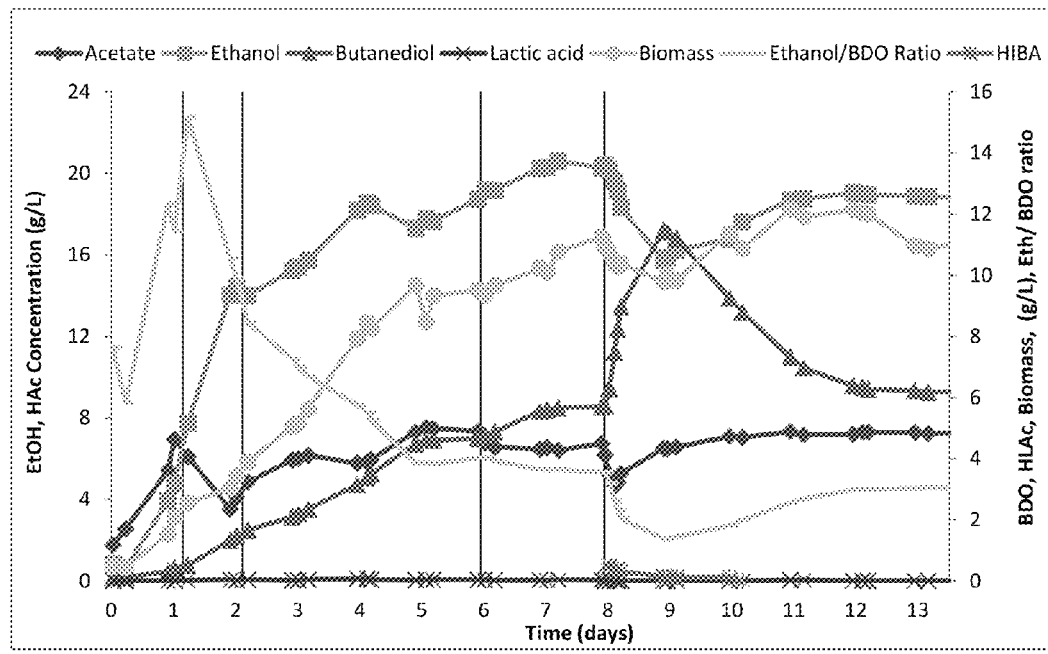
FIG. 1 shows the impact of 2-HIBA addition on the metabolite profile of a fermentation.

The present invention provides methods for the production of one or more products by the microbial fermentation of a gaseous substrate.

The gaseous substrate is selected from the group consisting of CO, CO2, H2, N2, CH4 and mixtures thereof. The invention provides methods for increasing production of one or more products derived from acetolactate.

DEFINITIONS

The term "products derived from acetolactate" or "acetolactate derived products" or similar terms as used herein are intended to encompass fermentation products having an acetolactate precursor. These products include but are not limited to 2,3-butanediol, 2-butanone, 2-butanol, and acetoin.

The term "branched chain amino acid" or similar terms are intended to encompass leucine, isoleucine, and valine.

The term "2,3-butanediol" should be interpreted to include all enantiomeric and diastereomeric forms of the compound, including (R,R), (S,S) and meso forms, in racemic, partially stereoisomerically pure and/or substantially stereoisomerically pure forms.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. As is described herein after, in some embodiments the bioreactor may comprise a first growth reactor and a second fermentation reactor. As such, when referring to the addition of a substrate, for example a substrate comprising carbon monoxide, to the bioreactor or fermentation reaction it should be understood to include addition to either or both of these reactors where appropriate.

The term "gaseous substrate" and/or "substrate" include any gas which contains a compound or element used by a microorganism as a carbon source and optionally energy source in fermentation. The gaseous substrate will typically contain a significant proportion of any of CO, CO2, CH4, H2 or mixtures thereof.

The term "substrate comprising carbon monoxide" and like terms should be understood to include any substrate in which carbon monoxide is available to one or more strains of bacteria for growth and/or fermentation, for example.

"Gaseous substrates comprising carbon monoxide" include any gas which contains a level of carbon monoxide.

The gaseous substrate will typically contain a major proportion of CO, preferably at least about 15% to about 95% CO by volume.

"Substrate comprising CO2" includes any substrate stream which contains a level of carbon dioxide. However, it should be appreciated that the gaseous substrate may be provided in alternative forms. For example, the gaseous substrate containing CO2 may be provided dissolved in a liquid. Essentially, a liquid is saturated with a carbon dioxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO2 and H2 may be adsorbed onto a solid support.

The term "product" as used herein is intended to encompass substances produced by the microbial fermentation. Product can include alcohols, acids or other chemicals. Products can also include gases produced by the microbial fermentation process.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated butanediol concentrations, the volume of desired product produced per volume of substrate consumed, the rate of production or level of production of the desired product, and the relative proportion of the desired product produced compared with other by-products of the fermentation.

The terms "productivity" or "rate of production" is the volumetric productivity of a product. In continuous systems the volumetric productivity is calculated as the ratio of the steady state concentration of the product and the liquid retention time. In batch systems the volumetric productivity is calculated as the concentration and the time required to produce said concentration in a batch system. The volumetric productivity is reported as g/L/day.

Unless the context requires otherwise, the phrases "fermenting", "fermentation process" or "fermentation reaction" and the like, as used herein, are intended to encompass both the growth phase and product biosynthesis phase of the process.

A "parental microorganism" is a microorganism used to generate a recombinant microorganism of the invention. The parental microorganism may be one that occurs in nature (i.e., a wild type microorganism) or one that has been previously modified but which does not express or over-express one or more of the enzymes the subject of the present invention. Accordingly, the recombinant microorganisms of the invention have been modified to express or over-express one or more enzymes that were not expressed or over-expressed in the parental microorganism.

The term "Exogenous" refers to nucleic acids which originate outside of the microorganism to which they are introduced. Exogenous nucleic acids may be derived from any appropriate source, including, but not limited to, the microorganism to which they are to be introduced (for example in a parental microorganism from which the recombinant microorganism is derived), strains or species of microorganisms which differ from the organism to which they are to be introduced, or they may be artificially or recombinantly created. "Exogenous" may also be used to refer to proteins. This refers to a protein that is not present in the parental microorganism from which the recombinant microorganism is derived.

The term "endogenous" as used in relation to a recombinant microorganism and a nucleic acid or protein refers to any nucleic acid or protein that is present in a parental microorganism from which the recombinant microorganism is derived.

"Over-express," "over expression," and like terms and phrases when used in relation to the invention should be taken broadly to include any increase in expression of one or more protein as compared to the expression level of the protein of a parental microorganism under the same conditions. It should not be taken to mean that the protein is expressed at any particular level.

While the following description focuses on particular embodiments of the invention, namely the production of 2,3-BDO using CO as the primary substrate, it should be appreciated that the invention may be applicable to production of alternative alcohols and/or acids and the use of alternative substrates as will be known by persons of ordinary skill in the art to which the invention relates. More particularly the invention may be applicable to the production of products derived from acetolactate using a gaseous substrate selected from the group consisting of CO, CO2, H2, CH4 and mixtures thereof.

Processes for microbial fermentation of gaseous substrates comprising carbon monoxide to produce products such as ethanol and acetate are widely known in the art. Such processes provide a means to produce commercially useful fuels from industrial waste gases comprising CO.

Accordingly, the inventors are the first to devise a process for producing high concentrations of 2,3-butanediol through the microbial fermentation of a gaseous substrate comprising CO. In a first stage, a gaseous substrate comprising CO is fed to a bioreactor containing a culture of one or more microorganisms suspending in liquid nutrient media. The gaseous substrate is anaerobically fermented to produce one or more alcohols and/or one or more acids or mixtures thereof. Compounds are provided to the fermentation to alter the metabolite profile of the fermentation.

The inventors demonstrated that the addition of 2-hydroxyiosbuytric acid (2-HIBA) to the bioreactor induces increased 2,3-BDO production. In particular embodiments, the process produces 2,3-BDO and ethanol. The ratio of 2,3-butanediol to ethanol produced by the method of the present invention is between 1:10 to 10:1 In particular embodiments, the process produces 2,3 Butanediol and ethanol at a ratio of 1:4, or, 1:3, or 1:2, or 1:1, or 1:2.

The inventors found that the addition of 2-HIBA to the fermentation at a concentration of between 0.01 g/L-2.0 g/L (0.096 to 19.2 mM) significantly increases the 2,3-BDO concentration. The addition of 2-HIBA is also shown to significantly improves the ethanol:2,3-BDO ratio.

The inventors have demonstrated that 2-HIBA can be added to a fermentation system in a continuous manner at concentrations of between 0.01 g/L/day-2.0 g/L/day (0.096 to 19.2 mM/day) to improve the ethanol:2,3-BDO ratio without affecting overall fermentation stability.

Figures 13, 14:
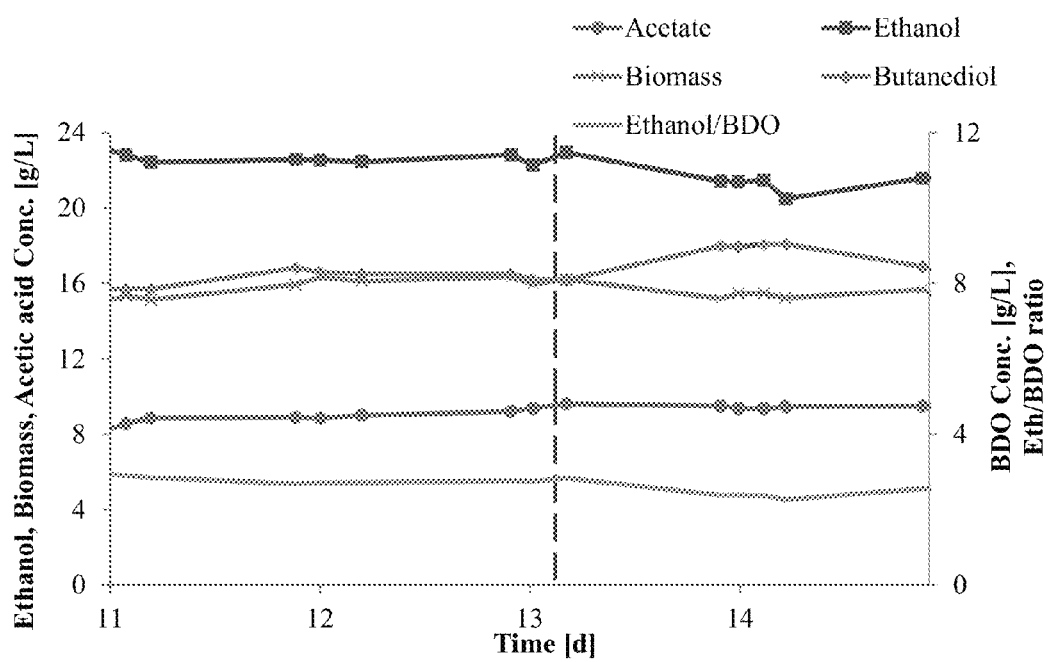
FIG. 13 shows the metabolite profile of a fermentation showing the impact of the addition of 15 mM 2-hydroxy-2methylbutyric acid.
FIG. 14: shows the comparative balance of carbon in a bioreactor before and after addition of 2-HIBA

Carbon balance measurements were performed to confirm the shift to increased 2,3-butanediol production after addition of 2-HIBA. Carbon balances showed a clear increase in 2,3-butanediol production, accompanied by a decrease in production of ethanol, acetate and biomass. FIG. 14 shows the comparative balance of carbon in a bioreactor before and after addition of 2-HIBA.

The inventors further found that 2-HIBA is not taken up or converted to products by the bacteria. 2-HIBA was demonstrated by the inventors to increase the production of 2,3-BDO and improve the ethanol:2,3-BDO ratio without being consumed by the fermentation. As the 2-HIBA is not consumed by the fermentation, it is possible to recover 2-HIBA exiting the bioreactor and pass it back to the bioreactor to improve the efficiency of the fermentation.

Figure 12:
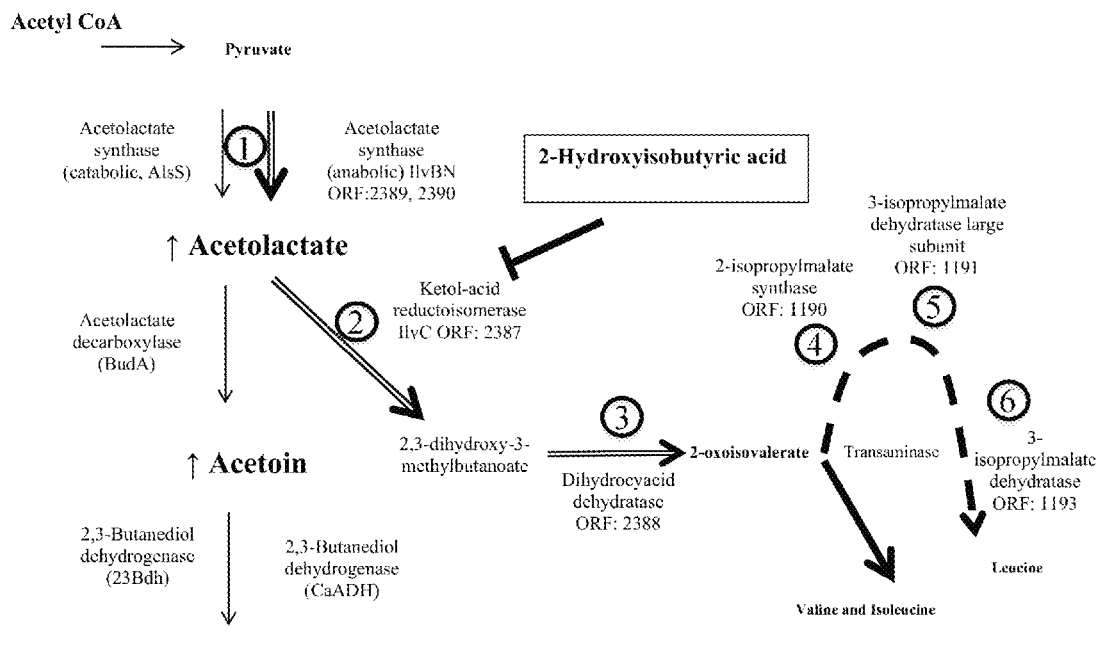
FIG. 12: schematic representation of the impact of 2-HIBA on the metabolism of LZ1561.

The addition of 2-HIBA impacts the metabolism of *Clostridium autoethanogenum*. FIG. 12 is a schematic representation which shows impact of 2-HIBA on the metabolism of *Clostridium autoethanogenum*. In native systems the expression and activity of Acetolcatate synthase IlvBN is down regulated by branched chain amino acid synthesis. The addition of 2-HIBA to the fermentation inhibits Ketol-acid recuctoisomerase IlvC, branch chained amino acid biosynthesis, which results in a decrease in the concentration of valine, isoleucine and leucine. As a result, feedback inhibition of the IlvBN enzyme by valine, isoleucine and leucine is removed. This causes an increase in acetolactate production. An increase in the acetolactate pool leads to an overflow of carbon to 2,3-butanediol. The conversion of acetolactate and acetoin to 2,3-BDO are not rate limited, and conversion to 2,3-BDO freely occurs without the need to further up regulate enzymes responsible for the conversion of acetolactate to acetoin and/or the conversion of acetoin to 2,3-BDO.

2-HIBA is a C4 carboxylic acid and an alpha hydroxy acid. It is a chemical compound that is not synthesised by *Clostridium autoethanogenum* and is rarely found in nature.

Ketol-acid reductoisomerase is inhibited by the presence of 2-HIBA. It is considered that other compounds having similar structural characteristics to 2-HIBA and the substrates that the enzyme works on (acetolactate. 2-oxo-3-hydroxyisovalerate and 2,3-dihydroxy-3-methylbutanoate) would have a similar effect on Ketol acid reductoisomerase. Inhibitors of ketol-acid reductoisomerase include compounds which inhibit one or more enzymes which convert acetolactate to branched chain amino acids. Typically the compounds inhibit ketol-acid reductoisomerase.

Typically, the compound comprises a carboxylic acid moiety, and the compound is substituted at the carbon atom alpha to the carboxylic acid moiety with an hydroxyl group or a carbonyl group. Preferably, the compound comprises a carboxylic acid moiety, and the compound is substituted at the carbon atom alpha to the carboxylic acid moiety with an hydroxyl group. More preferably, the compound comprises a carboxylic acid moiety, the compound is substituted at the carbon atom alpha to the carboxylic acid moiety with an hydroxyl group, and the compound is branched at the carbon atom alpha to the carboxylic acid moiety. By that is meant that in addition to the hydroxyl group bonded to the carbon atom alpha to the carboxylic acid moiety there are one or two non-hydrogen substituents also bonded to the carbon atom alpha to the carboxylic acid moiety.

Compounds of formula I containing one or more chiral centres may be used in enantiomerically pure form, or in the form of a mixture of isomers. For the avoidance of doubt, the compounds of formula I can, if desired, be used in the form of salts and/or solvates thereof. Further, for the avoidance of doubt, the compounds of the invention may be used in any tautomeric form.

Typical salt forms include salts with metals and amine compounds. Salts with metals may include salts with alkali metals (e.g. sodium or potassium) and alkali earth metals (e.g. calcium or magnesium). Salts with amines may include salts with alkyl amines, aralkyl amines and heterocyclic amines.

Typically, a $C_1$-$C_6$ alkyl group is a $C_1$-$C_4$ alkyl group, preferably a $C_1$-$C_3$ alkyl group, in some circumstances a $C_1$-$C_2$ alkyl group. Examples of a $C_1$-$C_6$ alkyl group include methyl, ethyl, n-propyl, i-propyl, n-butyl, i-butyl, s-butyl, t-butyl and hexyl. Methyl, ethyl and i-propyl groups are preferred. For the avoidance of doubt, where two alkyl moieties are present in a compound of formula (I), the alkyl moieties may be the same or different. Typically, alkyl moieties are unsubstituted.

A $C_1$-$C_6$ hydroxyalkyl group is typically a said $C_1$-$C_6$ alkyl group substituted by one or more hydroxyl (—OH) groups. Typically, it is substituted by 1, 2 or 3 hydroxyl groups, preferably 1 or 2, more preferably one hydroxyl group. Typically, a $C_1$-$C_6$ hydroxyalkyl group is a $C_1$-$C_4$ hydroxyalkyl group, preferably a $C_1$-$C_3$ hydroxyalkyl group. Preferred hydroxyalkyl groups are —C(OH)(CH$_3$)$_2$ groups. Typically, hydroxyalkyl groups are unsubstituted with groups other than the aforementioned hydroxyl groups.

Typically, $R_1$ is a straight or branched $C_1$-$C_4$ alkyl group, a straight or branched $C_1$-$C_4$ hydroxyalkyl group or a group —(C=O)R, where R is a straight or branched $C_1$-$C_4$ alkyl group. Preferably, $R_1$ is a straight or branched $C_1$-$C_3$ alkyl group, a straight or branched $C_1$-$C_3$ hydroxyalkyl group or a group —(C=O)R, where R is a straight or branched $C_1$-$C_3$ alkyl group. More preferably, $R_1$ is a straight or branched $C_1$-$C_3$ alkyl group, a branched $C_3$ hydroxyalkyl group or a group —(C=O)R, where R is a methyl group. Most preferably, $R_1$ is methyl, ethyl, i-propyl, a —C(OH)(CH$_3$)$_2$ group or a group —(C=O)R, where R is a methyl group.

Typically, $R_2$ is a hydrogen atom or a straight or branched $C_1$-$C_4$ alkyl group, a straight or branched $C_1$-$C_4$ hydroxyalkyl group or a group —(C=O)R, where R is a straight or branched $C_1$-$C_4$ alkyl group. Preferably, $R_2$ is a hydrogen atom or a straight or branched $C_1$-$C_3$ alkyl group or a straight or branched $C_1$-$C_3$ hydroxyalkyl group. More preferably $R_2$ is a hydrogen atom or a methyl or ethyl group. Most preferably, $R_2$ is a hydrogen atom or a methyl group.

Typically $R_1$ is a straight or branched $C_1$-$C_4$ alkyl group, a straight or branched $C_1$-$C_4$ hydroxyalkyl group or a group —(C=O)R, where R is a straight or branched $C_1$-$C_4$ alkyl group and $R_2$ is a hydrogen atom or a straight or branched $C_1$-$C_4$ alkyl group, a straight or branched $C_1$-$C_4$ hydroxyalkyl group or a group —(C=O)R, where R is a straight or branched $C_1$-$C_4$ alkyl group. Preferably $R_1$ is a straight or branched $C_1$-$C_3$ alkyl group, a straight or branched $C_1$-$C_3$ hydroxyalkyl group or a group —(C=O)R, where R is a straight or branched $C_1$-$C_3$ alkyl group and $R_2$ is a hydrogen atom or a straight or branched $C_1$-$C_3$ alkyl group or a straight or branched $C_1$-$C_3$ hydroxyalkyl group. More preferably $R_1$ is a straight or branched $C_1$-$C_3$ alkyl group, a branched $C_3$ hydroxyalkyl group or a group —(C=O)R, where R is a methyl group and $R_2$ is a hydrogen atom or a methyl or ethyl group. Most preferably $R_1$ is methyl, ethyl, i-propyl, a —C(OH)(CH$_3$)$_2$ group or a group —(C=O)R, where R is a methyl group and $R_2$ is a hydrogen atom or a methyl group.

Typically, $R_1$ and $R_2$ are not both a group —(C=O)R as defined above. Typically, $R_1$ and $R_2$ are not both a $C_1$-$C_6$ hydroxyalkyl group as defined above. Thus, typically, $R_1$ is as defined above; and $R_2$ is a hydrogen atom or a straight or branched $C_1$-$C_6$ alkyl group, preferably a hydrogen atom or a straight or branched $C_1$-$C_4$ alkyl group, more preferably a hydrogen atom or a methyl or ethyl group, most preferably a hydrogen atom or a methyl group.

In certain circumstances it may be preferably that both $R_1$ and $R_2$ are alkyl groups. In this instance, $R_1$ is a straight or branched $C_1$-$C_6$ alkyl group and $R_2$ is a straight or branched $C_1$-$C_6$ alkyl group. Preferably, $R_1$ is a straight or branched $C_1$-$C_4$ alkyl group and $R_2$ is a straight or branched $C_1$-$C_4$ alkyl group. More preferably, $R_1$ is a straight or branched $C_1$-$C_3$ alkyl group and $R_2$ is a straight or branched $C_1$-$C_3$ alkyl group. Even more preferably, $R_1$ is a methyl or ethyl group and $R_2$ is a methyl or ethyl group. Most preferably, $R_1$ and $R_2$ are methyl groups.

Particularly preferred compounds of formula I are 2-hydroxyisobutyric acid, 2-hydroxyl-2-methylbutyric acid, 2-hydroxybutyrate and 2-hydroxy-3-methylbutyric acid. 2-hydroxyisobutyric acid is especially preferred. Thus, particularly preferred compounds of formula I are typically chosen from the following compounds:

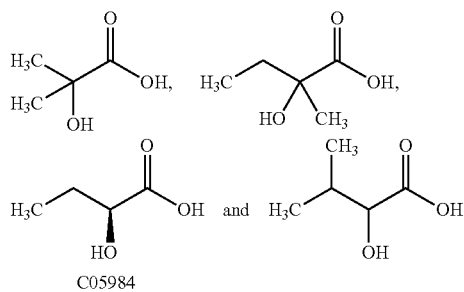

Typically, $R_3$ is a straight or branched $C_1$-$C_4$ alkyl group or a straight or branched $C_1$-$C_4$ hydroxyalkyl group. Preferably, $R_3$ is a straight or branched $C_1$-$C_3$ alkyl group or a straight or branched $C_1$-$C_3$ hydroxyalkyl group. Most preferably, $R_3$ is i-propyl or —C(OH)(CH$_3$)$_2$. Particularly preferred compounds of formula II are 2-keto-3-hydroxyisovalerate and 2-ketoisovalerate. Thus, particularly preferred compounds of formula II are typically chosen from the following compounds:

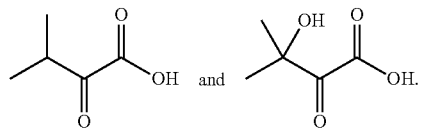

Examples of ketol acid reductoisomerase inhibitors include, but are not limited to Keto β hydroxyisovalerate, hydroxybutyrate, hydroxyl α methylbutyrate, hydroxyisovalerate, keto isovalerate (Arfin et al, Purification and Properties of the Acetohydroxy Acid Isomeroreductase of *Salmonella typhimurium*. The Journal of Biomedical Chemistry 1969, Vol. 244, No. 5, pp 1118-1127.) and oxalyl hydroxamates (Aulabaugh et al, Oxalyl Hydroxamates as Reaction-Intermediate Analogues for Ketol-Acid Reductoisomerase, Biochemistry 1990, 29, pp 2824-2830). Further examples of compounds that effect the IlvC pathway include, 2-hydroxyl-2-methylbutyric acid, 2-hydroxybutyrate, 2-hydroxy-3-methylbutyric acid, 2-keto-3-hydroxyisovalerate and 2-ketoisovalerate.

The addition of one or more of the inhibitory compounds discussed to the fermentation increases the production of acetolactate by the above described mechanism of branched chain amino acid production inhibition. The increase in the acetolactate pool results in an increase flow of carbon to other acetolactate derived products, including 2,3-butanediol.

An inhibitory compound is added to the liquid nutrient medium in concentrations sufficient to elicit an inhibitory response on the production of branched chain amino acids, and increase the production of other products derived from acetolactate. The compound may be added to the liquid nutrient medium in a continuous manner at concentrations of between 0.05 mM and 50 mM. The amount of an acetolactate derived product produced by the addition of the compound to the fermentation compared to a fermentation without addition of the compound is at least about 10% higher, at least about 20% higher, at least about 30% higher, at least about 40% higher, at least about 50% higher, at least about 60% higher, at least about 70% higher, at least about 80% higher, at least about 90% higher, at least about 100% higher, at least about 110% higher, at least about 120% higher, at least about 130% higher, at least about 140% higher, at least about 150% higher.

The fermentation may be carried out in any suitable bioreactor, such as an immobilised cell reactor, a gas-lift reactor, a bubble column reactor (BCR), a membrane reactor, such as a Hollow Fibre Membrane Bioreactor (HFM BR) or a trickle bed reactor (TBR). Also, in some embodiments of the invention, the bioreactor may comprise a first growth reactor in which the micro-organisms are cultured, and a second fermentation reactor, to which fermentation broth from the growth reactor may be fed and in which most of the fermentation product (e.g. ethanol and acetate) may be produced. The bioreactor of the present invention is adapted to receive a gaseous substrate selected from the group consisting of CO, CO2, H2 and mixtures thereof.

In particular embodiments, the microorganism is a carboxydotrophic bacteria. In various embodiments, the carboxydotrophic microorganism is selected from *Clostridium, Moorella, Oxobacter, Peptostreptococcus, Acetobacterium, Eubacterium*, or *Butyribacterium*. In various embodiments, the microorganism is selected from the group comprising *Clostridium autoethanogenum, Clostridium ljungdahli, Clostridium carboxidivorans, Clostridium drakei, Clostridium scatologenes, Clostridium aceticum, Clostridium formicoaceticum, Clostridium magnum, Butyribacterium methylotrphoicum, Acetobacterium woodii, Alkalibaculum bacchi, Blautia producta, Eubacterium limosum, Moorella thermoacetica, Sporomusa ovata, Sporomusa silvacetica, Sporomusa sphaeroides, Oxobacter pfennigii* and *Thermoanaerobacter kiuvi*.

In particular embodiments, the microorganism is *Clostridium autoethanogenum* or *Clostridium ljungdahlii*. In one particular embodiment, the microorganism is *Clostridium autoethanogenum*. In a particular embodiment, the microorganism has the identifying characteristics of accession number DSMZ10061 or DSMZ23693.

Recombinant Microorganism for Inhbiting BCAA Synthesis

One aspect of the invention is the provision of carboxydotrophic acetogenic microorganisms which have reduced ability to convert carbonaceous gaseous substrates to branched chain amino acids. An enzyme which is a ketol-acid reductoisomerase can be inactivated by mutation to reduce, partially or totally, its activity. If the microorganisms naturally or by modification have the ability to produce useful carbon-containing compounds derived from acetolactate, reducing the ability of the ketol-acid reductoisomerase will lead to accumulation of the useful compound.

Referring to FIG. 12, the expression and activity of Acetolcatate synthase IlvBN is down regulated by branched chain amino acids. The inhibition of Ketol-acid reuctoisomerase IlvC, an enzyme catalyzing a step in branched chained amino acid biosynthesis, results in a decrease in the production of valine, isoleucine and leucine. As a result, expression of IlvBN encoding genes is activated and feedback inhibition of the IlvBN enzyme by branched chain amino acids is removed. This causes an increase in the acetolactate production. An increase in the acetolactate pool leads to an increased flux of carbon to products derived from acetolactate, including 2,3-butanediol, acetoin, 2-butanol and 2-butanone.

Microorganisms which can be modified according to the invention include any which can make an acetolactate-derived product, such as acetoin, butanediol, butanone, and 2-butanol. The microorganism must also have a gene for ketol-acid reductoisomerase. The ketol-acid reductoisomerase may have an amino acid sequence according to SEQ ID NO: 1.

Inactivating mutations may be made by any means known in the art for that particular microorganism. Chemical mutagenesis, transposon mutagenesis, viral mutagenesis, in vitro mutagenesis, are exemplary means. Inactivating mutations may partially reduce or totally eliminate activity of the ketol-acid reductoisomerase. These may be insertions, deletions, substitutions, or nonsense mutations, for example. The mutations may reduce the enzyme activity of the microorganism by at least 10%, at least 20%, at least 30%, at least 40%, at least 50%, at least 60%, at least 70%, at least 80%, or at least 90%. This may be done by reducing enzyme activity per se, or reducing the amount of enzyme.

In certain embodiments, the activity of ketol-acid reductoisomerase may be totally inactivated, as for example in the case of gene knockouts. If the activity of ketol-acid reductoisomerase is totally inactivated, it is necessary to supplement the fermentation with branched chain amino acids or their immediate biological precursors.

Recombinant Microorganisms for Increasing Acetolactate Synthesis

One aspect of the invention is the provision of a carboxydotrophic acetogenic microorganism comprising one or more genetic modification which is adapted to increase the level of acetolactate synthase activity. Upon growth on and/or fermentation of a gaseous carbonaceous substrate, the microorganism produces an increased amount of acetolactate compared to a parental microorganism, The acetolactate synthase may have an amino acid sequence according to SEQ ID NO: 2

An "acetolactate synthase" is meant to include both catabolic acetolactate synthase enzymes and anabolic acetolactate (or acetohydroxy acid) synthase enzymes.

The one or more genetic modification which is adapted to increase the level of acetolactate synthase may comprise, the overexpression of an endogenous catabolic acetolactate synthase, the expression of an exogenous catabolic acetolactate synthase, the expression of an exogenous anabolic acetolactate synthase, the overexpression of an endogenous anabolic acetolactate synthase, the substitution of an endogenous acetolactate synthase with an exogenous catabolic acetolactate synthase, the substitution of an endogenous acetolactate synthase with an exogenous anabolic acetolactate synthase, or the overexpression of a subunit of an endogenous anabolic synthase, said subunit being insensitive to feedback inhibition by branched chain amino acids.

A "genetic modification which is adapted to increase acetolactate synthase activity" as mentioned herein before should be taken broadly to include any genetic modification which at least increases acetolactate synthase expression, acetolactate biosynthesis, acetolactate synthase function and/or the level of acetolactate synthase activity. The phrase should be taken to include, for example: modification of a gene encoding one or more acetolactate synthase; modification to a genetic regulatory element involved in the expression of a gene encoding acetolactate synthase; introduction of a nucleic acid encoding a acetolactate synthase; introduction of a nucleic acid which produces (or increases the level of expression, activity or the function of) a protein which increases acetolactate synthase expression, acetolactate biosynthesis, acetolactate synthase function and/or the level of acetolactate synthase activity. Skilled persons will readily appreciate other genetic modifications which may be made to achieve an increase in acetolactate synthase activity.

Incorporated by reference in its entirety herein is a computer-readable nucleotide/amino acid sequence listing submitted concurrently herewith and identified as follows: ASCII (text) file named "LT97_ST25.txt" created on 18 Sep. 2014

Microorganisms which may be modified include but are not limited to acetogenic, carboxydotrophic bacteria, such as *Clostridium* species, *C. autoethanogenum*, *C. ljungdahlii*, and *C. ragsdalei*. Other carboxydotrophic microorganisms which might be used include *Clostridium carboxidovirans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kiuvi*. In one particular embodiment, the microorganism is selected from the group consisting of *E. coli*, *Saccharomyces cerevisiae*, *Clostridium acetobutylicum*, *C. beijerinckii*, *C. saccharbutyricum*, *C. saccharoperbutylacetonicum*, *C. butyricum*, *C. diolis*, *C. kluyveri*, *C. pasterianium*, *C. novyi*, *C. difficile*, *C. thermocellum*, *C. cellulolyticum*, *C. cellulovorans*, *C. phytofermentans*, *Lactococcus lactis*, *Bacillus subtilis*, *Bacillus licheniformis*, *Zymomonas mobilis*, *Klebsiella oxytoca*, *Klebsiella pneumonia*, *Corynebacterium glutamicum*, *Trichoderma reesei*, *Ralstonia eutropha*, *Pseudomonas putida*, *Lactobacillus plantarum*. Other bacteria which may be modified according to the invention include those from the genus *Escherichia*, *Saccharomyces*, *Clostridium*, *Bacillus*, *Lactococcus*, *Zymomonas*, *Corynebacterium*, *Pichia*, *Candida*, *Hansenula*, *Trichoderma*, *Acetobacterium*, *Ralstonia*, *Salmonella*, *Klebsiella*, *Paenibacillus*, *Pseudomonas*, *Lactobacillus*, *Rhodococcus*, *Enterococcus*, *Alkaligenes*, and *Brevibacterium*.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

Fermentation

Processes for the production of ethanol and other alcohols from gaseous substrates (such as those described in the background section above) are known. Exemplary processes include those described for example in WO 2007/117157 and WO 2008/115080, as well as U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of gaseous substrate to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and *Clostridium autoethanogenum* (Abrini et al., Archives of Microbiology 161: pp 345-351). Other suitable bacteria include those of the genus *Moorella*, including *Moorella* sp $HUC_{22}$-1 (Sakai et al., Biotechnology Letters 29: pp 1607-1612), and those of the genus *Carboxydothermus* (Svetlichny, V. A., et al. (1991), Systematic and Applied Microbiology 14: 254-260). The disclosures of each of these publications are incorporated herein by reference. In addition, other carboxydotrophic anaerobic bacteria can be used in the processes of the invention by a person of skill in the art. It will also be appreciated upon consideration of the instant disclosure that a mixed culture of two or more bacteria may be used in processes of the present invention.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

In one embodiment, the microorganism or parental microorganism is selected from the group of carboxydotrophic Clostridia comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*. In a further embodiment, the microorganism is from the cluster of carboxydotrophic Clostridia comprising the species *C. autoethanogenum*, *C. ljungdahlii*, and *C. ragsdalei* and related isolates. These include but are not limited to strains *C. autoethanogenum* JAI-1T (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETCT (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* 0-52 (ATCC 55989) (U.S. Pat. No. 6,368,819), *C. ragsdalei* P11T (ATCC BAA-622) (WO 2008/028055), related isolates such as "*C. coskatii*" (US20110229947) and "*Clostridium* sp." (Tyurin & Kiriukhin, 2012), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055).

All species of the above-referenced cluster have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions (Abrini et al., 1994; Köpke et al., 2011; Tanner et al., 1993) (WO 2008/028055). Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not. The organization and number of Wood-Ljungdahl pathway genes, responsible for gas uptake, has been found to be the same in all species, despite differences in nucleic and amino acid sequences (Köpke et al., 2011). Also reduction of carboxylic acids into their corresponding alcohols has been shown in a range of these organisms (Perez, Richter, Loftus, & Angenent, 2012). These traits are therefore not specific to one organism like *C. autoethanogenum* or *C. ljungdahlii*, but rather general traits for carboxydotrophic, ethanol-synthesizing Clostridia and it can be anticipated that mechanism work similar across these strains, although there may be differences in performance (Perez et al., 2012).

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSM 10061.

The fermentation may be carried out in any suitable bioreactor. In some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

The Gaseous Substrate

The CO Containing Substrate

A substrate comprising carbon monoxide, preferably a gaseous substrate comprising carbon monoxide, is used in the fermentation reaction to produce ethanol in the methods of the invention. The gaseous substrate may be a waste gas obtained as a by-product of an industrial process, or from some other source such as from combustion engine (for example automobile) exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method.

Depending on the composition of the gaseous substrate comprising carbon monoxide, it may also be desirable to treat it to remove any undesired impurities, such as dust particles before introducing it to the fermentation. For example, the gaseous substrate may be filtered or scrubbed using known methods.

In other embodiments of the invention, the gaseous substrate comprising carbon monoxide may be sourced from the gasification of biomass. The process of gasification involves partial combustion of biomass in a restricted supply of air or oxygen. The resultant gas typically comprises mainly CO and Hz, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 15% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

The gaseous substrate may also contain some $CO_2$ for example, such as about 1% to about 80% by volume, or 1% to about 30% by volume. In one embodiment it contains about 5% to about 10% by volume. In another embodiment the gaseous substrate contains approximately 20% $CO_2$ by volume.

Typically, the carbon monoxide will be added to the fermentation reaction in a gaseous state. However, the invention should not be considered to be limited to addition of the substrate in this state. For example, the carbon monoxide could be provided in a liquid. For example, a liquid may be saturated with a carbon monoxide containing gas and then that liquid added to a bioreactor. This may be achieved using standard methodology. By way of example, a microbubble dispersion generator (Hensirisak et. al. Scale-up of microbubble dispersion generator for aerobic fermentation; *Applied Biochemistry and Biotechnology Volume* 101, *Number 3/October,* 2002) could be used.

In one embodiment of the invention, a combination of two or more different substrates may be used in the fermentation reaction.

In addition, it is often desirable to increase the CO concentration of a substrate stream (or CO partial pressure in a gaseous substrate) and thus increase the efficiency of fermentation reactions where CO is a substrate. Increasing CO partial pressure in a gaseous substrate increases CO mass transfer into a fermentation media. The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

The H2 and CO2 Containing Substrate

A substrate comprising Carbon dioxide and Hydrogen is used in the fermentation reaction to produce acetate in accordance with certain embodiments of the invention. The gaseous substrate may be a waste gas obtained as a by-product of an industrial process, as discussed above in relation to the CO containing substrate. A skilled addressee would understand that the $CO_2$ producing process is not limited to those discussed. $CO_2$ and $H_2$ can be derived from any suitable source. The $CO_2$ and $H_2$ can be derived from the same source, or alternatively the CO2 and H2 can be derived from different sources and then blended to produce a substrate comprising CO2 and H2.

The substrate comprising CO2 and H2 may comprise at least 5% CO2 by volume, at least 10% CO2 by volume, at least 15% CO2 by volume, at least 20% CO2 by volume, at least 30% CO2 by volume or at least 40% CO2 by volume. Substrates having higher concentration of CO2, such as at least 70% by volume may also be appropriate.

The substrate comprising CO2 and H2 may comprise at least 30% H2 by volume, at least 40% H2 by volume, at least 50% H2 by volume, at least 60% H2 by volume, at least 70% H2 by volume or at least 80% H2 by volume. Substrates having lower concentrations of H2 such as around 5% H2 by volume, or around 10% H2 by volume, or around 15% H2 by volume, or around 20% H2 by volume, mal also be appropriate.

Industrial Off Gas as a Resource for Fermentation

In accordance with other aspects of the invention, industrial waste gases are used in a fermentation reaction with no or only minimal additional scrubbing or pre-treatment steps being used to make the gases suitable therefor.

The waste gases may result from any number of industrial processes. The invention has particular applicability to supporting the production of ethanol from gaseous substrates such as high volume CO2/H2-containing industrial flue gases. Examples include gases produced during ferrous metal products manufacturing, non-ferrous products manufacturing, refinery processes, petroleum refining processes, gasification of coal, gasification of biomass, electric power production, carbon black production, ammonia production, methanol production and coke manufacturing. In certain embodiments the CO2/H2 containing substrate is derived from gasification of biomass or municipal solid waste. In a particular embodiment of the invention, the waste gases are generated during a process for making steel. For example, those skilled in the art will appreciate the waste gases produced during various stages of the steel making process have high CO2 and H2 concentrations.

Waste gases produced during the carburisation of steel are optionally passed through water to remove particulate matter before passing to a waste stack or flue for directing the waste gas into the atmosphere. Typically, the gases are driven into the waste stack with one or more fans.

In particular embodiments of the invention, at least a portion of the waste gas produced during the decarburisation of steel is diverted to a fermentation system by suitable conduit means. By way of example, piping or other transfer means can be connected to the waste gas stack from a steel mill to divert at least a portion of the waste gas to a fermentation system. Again, one or more fans can be used to divert at least a portion of the waste gas into the fermentation system. In particular embodiments of the invention, the conduit means is adapted to provide at least a portion of the waste gas produced during the decarburisation of steel to a fermentation system. The control of and means for feeding gases to a bioreactor will be readily apparent to those of ordinary skill in the art to which the invention relates.

While steel mills can be adapted to substantially continuously produce steel and subsequently waste gases, particular aspects of the process may be intermittent. Typically the decarburisation of steel is a batch process lasting several minutes to several hours. As such, the conduit means may be adapted to divert at least a portion of the waste gas, such as the gas produced during the decarburisation of steel, to the fermentation system if it is determined the waste gas has a desirable composition.

The pH of the contents of the bioreactor used in the fermentation process may be adjusted as required. The appropriate pH will be dependent on the conditions required for a particular fermentation reaction having regard to the nutrient media and micro-organisms used, as will be appreciated by persons of ordinary skill in the art to which the invention relates. In one preferred embodiment, in fermentation of a gaseous substrate containing CO2 utilising *Clostridium autoethanogenum*, the pH may be adjusted to approximately 4.5 to 6.5. Further examples include pH 5.5 to 6.5 using *Moorella thermoacetica* for the production of acetic acid, pH 4.5 to 6.5 using *Clostridium acetobutylicum* for the production of butanol, and pH 7 using *Carboxydothermus hygrogenaformans* for the production of hydrogen. Those skilled in the art will be aware of suitable means for maintaining the bioreactor at the required pH. However, by way of example, aqueous bases such as NaOH and aqueous acids such as H2SO4 can be used to raise and lower the pH of the fermentation medium and maintain the desired pH.

An additional benefit of the invention is that, because there is no or only minimal scrubbing and/or other treatment processes performed on the waste gases prior to their use in a fermentation reaction, the gases will contain additional material resulting from the industrial process, which additional material may be used, at least in part, as a feedstock for the fermentation reaction.

Syngas derived from natural gas may also be used in the fermentation process. There are a number of known methods for reforming a natural gas stream to produce syngas. The end use of the syngas can determine the optimal syngas properties. The type of reforming method, and the operating conditions used determines the syngas concentration. As such syngas composition depends on the choice of catalyst, reformer operating temperature and pressure, and the ratio of natural gas to $CO_2$, $H_2O$ and/or $O_2$ or any combination of $CO_2$, $H_2O$ and $O_2$. It would be understood to a person skilled in the art that a number of reforming technologies can be used to achieve a syngas with a desired composition.

Blending of Streams

It may be desirable to blend a reformed substrate stream comprising CO and H2 with one or more further streams in order to improve efficiency, alcohol production and/or overall carbon capture of the fermentation reaction. Without wishing to be bound by theory, in some embodiments of the present invention, carboxydotrophic bacteria convert CO to ethanol according to the following:

$$6CO + 3H_2O \rightarrow C_2H_5OH + 4CO_2$$

However, in the presence of H2, the overall conversion can be as follows:

$$6CO + 12H_2 \rightarrow 3C_2H_5OH + 3H_2O$$

Accordingly, streams with high CO content can be blended with reformed substrate streams comprising CO and H2 to increase the CO:H2 ratio to optimise fermentation efficiency. By way of example, industrial waste streams, such as off-gas from a steel mill have a high CO content, but include minimal or no H2. As such, it can be desirable to blend one or more streams comprising CO and H2 with the waste stream comprising CO, prior to providing the blended substrate stream to the fermenter. The overall efficiency, alcohol productivity and/or overall carbon capture of the fermentation will be dependent on the stoichiometry of the CO and H2 in the blended stream. However, in particular embodiments the blended stream may substantially comprise CO and H2 in the following molar ratios: 20:1, 10:1, 5:1, 3:1, 2:1, 1:1 or 1:2.

In addition, it may be desirable to provide CO and H2 in particular ratios at different stages of the fermentation. For example, substrate streams with a relatively high H2 content (such as 1:2 CO:H2) may be provided to the fermentation stage during start up and/or phases of rapid microbial growth. However, when the growth phase slows, such that the culture is maintained at a substantially steady microbial density, the CO content may be increased (such as at least 1:1 or 2:1 or higher, wherein the H2 concentration may be greater or equal to zero).

Blending of streams may also have further advantages, particularly in instances where a waste stream comprising CO is intermittent in nature. For example, an intermittent waste stream comprising CO may be blended with a substantially continuous reformed substrate stream comprising CO and H2 and provided to the fermenter. In particular embodiments of the invention, the composition and flow rate of the substantially continuous blended stream may be varied in accordance with the intermittent stream in order to maintain provision of a substrate stream of substantially continuous composition and flow rate to the fermenter.

Media

It will be appreciated that for growth of the one or more microorganisms and substrate to ethanol and/or acetate fermentation to occur, in addition to the substrate, a suitable nutrient medium will need to be fed to the bioreactor. A nutrient medium will contain components, such as vitamins and minerals, sufficient to permit growth of the micro-organism used. By way of example only, anaerobic media suitable for the growth of *Clostridium autoethanogenum* are known in the art, as described for example by Abrini et al (*Clostridium autoethanogenum*, sp. Nov., An Anaerobic Bacterium That Produces Ethanol From Carbon Monoxide; *Arch. Microbiol.*, 161: 345-351 (1994)). The "Examples" section herein after provides further examples of suitable media.

The Bioreactor

The fermentation may be carried out in any suitable bioreactor, such as an immobilised cell reactor, a gas-lift reactor, a bubble column reactor (BCR), a membrane reactor, such as a Hollow Fibre Membrane Bioreactor (HFM BR) or a trickle bed reactor (TBR). Also, in some embodiments of the invention, the bioreactor may comprise a first growth reactor in which the micro-organisms are cultured, and a second fermentation reactor, to which fermentation broth from the growth reactor may be fed and in which most of the fermentation product (e.g. ethanol and acetate) may be produced. The bioreactor of the present invention is adapted to receive a CO2, H2 and optionally CO containing substrate.

Fermentation

Processes for the production of ethanol and other alcohols from gaseous substrates are known. Exemplary processes include those described for example in WO2007/117157, WO2008/115080, WO2009/022925, WO2009/064200, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

Fermentation Conditions

The fermentation should desirably be carried out under appropriate conditions for the substrate to ethanol and/or acetate fermentation to occur. Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in general, it is preferred that the fermentation be performed at a pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-product conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-product fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

Examples of fermentation conditions suitable for anaerobic fermentation of a substrate comprising CO are detailed in WO2007/117157, WO2008/115080, WO2009/022925 and WO2009/064200. It is recognised the fermentation conditions reported therein can be readily modified in accordance with the methods of the instant invention.

Fermentation Products

Methods of the invention can be used to produce any of a variety of hydrocarbon products. This includes alcohols, acids and/or diols. More particularly, the invention may be applicable to fermentation to produce butyrate, propionate, caproate, ethanol, propanol, butanol, 2,3-butanediol, propylene, butadiene, iso-butylene and ethylene. In one embodiment the invention can be used to produce alcohols including but not limited to propanol and butanol. The alcohol(s) can then be reacted with acetate to produce product(s) including propyl acetate or butyl acetate. A skilled person would understand that the invention is not limited to the alcohols and products mentioned, any appropriate alcohol and or acid can be used to produce a product.

These and other products may be of value for a host of other processes such as the production of plastics, pharmaceuticals and agrochemicals. In one embodiment, the fermentation product is used to produce gasoline range hydrocarbons (about 8 carbon), diesel hydrocarbons (about 12 carbon) or jet fuel hydrocarbons (about 12 carbon).

The methods of the invention can also be applied to aerobic fermentations, to anaerobic or aerobic fermentations of other products, including but not limited to isopropanol. The methods of the invention can also be applied to aerobic fermentations, and to anaerobic or aerobic fermentations of other products, including but not limited to isopropanol.

The invention also provides that at least a portion of a hydrocarbon product produced by the fermentation is reused in the steam reforming process. This may be performed because hydrocarbons other than $CH_4$ are able to react with steam over a catalyst to produce $H_2$ and CO. In a particular embodiment, ethanol is recycled to be used as a feedstock for the steam reforming process. In a further embodiment, the hydrocarbon feedstock and/or product is passed through a prereformer prior to being used in the steam reforming process. Passing through a prereformer partially completes the steam reforming step of the steam reforming process which can increase the efficiency of hydrogen production and reduce the required capacity of the steam reforming furnace.

The methods of the invention can also be applied to aerobic fermentations, and to anaerobic or aerobic fermentations of other products, including but not limited to isopropanol.

More particularly, the invention may be applicable to fermentation to ethanol and/or acetate. These products may then be reacted to together to produce chemical products including esters. In one embodiment of the invention the ethanol and acetate produced by fermentation are reacted together to produce Ethyl Acetate. Ethyl acetate may be of value for a host of other processes such as the production of solvents including surface coating and thinners as well as in the manufacture of pharmaceuticals and flavours and essences.

Product Recovery

The products of the fermentation reaction can be recovered using known methods. Exemplary methods include those described in WO07/117157, WO08/115080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non-volatile and is recovered for re-use in the fermentation.

Acetate, which may be produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Biomass recovered from the bioreactor may undergo anaerobic digestion in a digestion. to produce a biomass product, preferably methane. This biomass product may be used as a feedstock for the steam reforming process or used to produce supplemental heat to drive one or more of the reactions defined herein.

General

Embodiments of the invention are described by way of example. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the substrate and/or exhaust streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. One or more processors may be incorporated into the system to regulate and/or control particular parameters of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of $CO_2$ or $H_2$ or high levels of $O_2$ that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used. For example, heat exchangers may be employed to heat or cool the substrate streams.

Furthermore, the system may include one or more pre/post treatment steps to improve the operation or efficiency of a particular stage. For example, a pre-treatment step may include means for removing particulate matter and/or long chain hydrocarbons or tars from a gaseous substrate stream. Other pre- or post-operations that may be conducted include separation of desired product(s) from particular stages, such as, for example, the bioreactor production stage (e.g. removal of ethanol by distillation).

The invention will now be described, by way of example only, with reference to the following Examples.

EXAMPLES

Materials and Methods

TABLE 1

Fermentation media

| Media Component | Concentration (mM/L) |
|---|---|
| MgCl$_2$ 6H$_2$O | 2 |
| NaCl | 2 |
| CaCl$_2$ 6H$_2$O | 2 |
| KCl | 25 |
| H$_3$PO$_4$ 85% | 0.375 mL |
| Trace metal | 7.5 mL |
| B-vitamins | 20 mL |

| Trace metal composition | Final concentration in the media (µmol/L) | Concentration (mM/L) 200 × stock solution |
|---|---|---|
| FeCl$_2$ 4H$_2$O | 150 | 20 |
| CoCl$_2$ 6H$_2$O | 7.5 | 1 |
| ZnCl$_2$ | 7.5 | 1 |
| H$_3$BO$_3$ | 3 | 0.4 |
| MnCl$_2$ 4H$_2$O | 3 | 0.4 |
| Na$_2$MoO$_4$ 2H$_2$O | 3 | 0.4 |
| NiCl$_2$ 6H$_2$O | 3 | 0.4 |
| Na$_2$WO$_4$ 2H$_2$O | 3 | 0.4 |
| Na$_2$SeO$_3$ | 3 | 0.4 |

| Vitamin | Final concentration in the media (mg/L) | Concentration (mg/L) 100 × stock solution |
|---|---|---|
| Thiamine hydrocloride (B1) | 1 | 50 |
| Riboflavin (B2) | 1 | 50 |
| Nicotinic acid (B3) | 1 | 50 |
| Pantothenic acid (B5) | 1 | 50 |
| Pyridoxine hydrochloride (B6) | 0.2 | 10 |
| Biotin (B7) | 0.4 | 20 |
| Folic acid (B9) | 0.2 | 10 |
| 4-Aminobenzoic acid (PABA or B10) | 1 | 50 |
| Cyanocobalamin (B12) | 1 | 50 |
| Lipoic acid (Thiotic acid) | 1 | 50 |

Bioreactor Medium Preparation:

Fermentations with *C. autoethanogenum* DSM23693 were carried out in 1.5 L bioreactors at 37° C. The media was prepared according to Table 1. To achieve anaerobicity the reactor vessel was sparged with nitrogen. Prior to inoculation, the gas was switched to either steel mill gas containing H$_2$ (3%), N$_2$ (30%), CO (47%) and CO$_2$ (20%) or pure gases (50% CO, 18-40% CO$_2$, with the balance N$_2$). The gas flow was initially set at 67 ml/min/L, increasing to 200 ml/min during mid-exponential phase, while the agitation was increased from 200 rpm to 800. Na$_2$S was dosed into the bioreactor at 0.25 ml/hr. Once the OD600 reached 1.5, the bioreactor was switched to a continuous mode at a dilution rate of 2.0-1.6 d-l and a bacterial dilution rate of 0.9-0.6 d-l. During continuous mode gas and agitation were adjusted to 900-950 rpm and 800-900 ml/min. Na$_2$S was increased to 1.0 ml/hr.

Sampling and Analytical Procedures:

Liquid culture samples were taken at differing intervals over the duration of the fermentation. These samples were used to establish the optical density at 600 nm (spectrophotometer) and the level of substrates and products (high performance liquid chromatography—HPLC). HPLC was routinely used to quantify the level of acetate, ethanol and 2,3-butanediol. The input and output gas compositions were analysed using a gas chromatographer (GC), allowing measurement of CO and H$_2$ consumption and CO$_2$ production by the culture.

Example 1

The impacts of 2-HIBA were investigated on a single reactor system which had been optimised for 2,3-BDO production. This was done to ascertain the impact that this chemical would have on a high performance system and obtain information on suitable concentrations that would not interfere with overall fermentation stability. 0.5 g/L (4.8 mM) 2-HIBA was added to the fermenter on day 7.95, the results from this addition are shown in FIG. 1. The addition of 2-HIBA altered the metabolite profile of the fermentation increasing the production of 2,3-butanediol whilst decreasing the production of ethanol, acetate and biomass.

Figure 2:
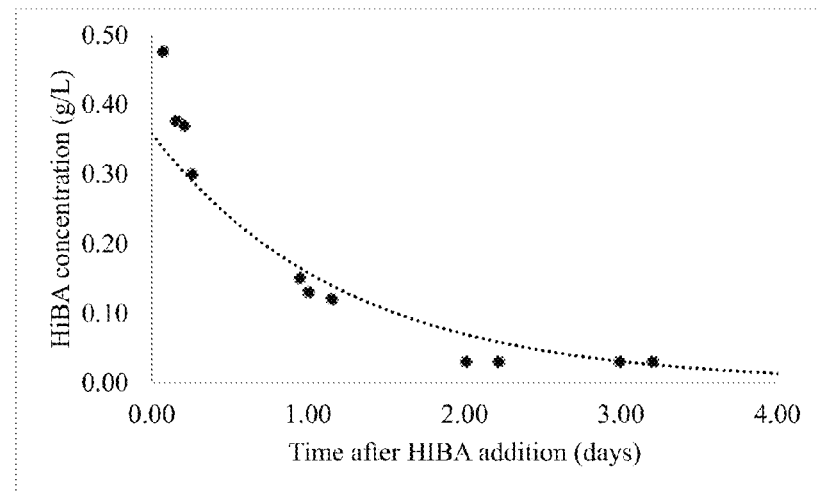
FIG. 2 shows an exponential washout curve of 2-HIBA based on the liquid dilution rate and the bacterial dilution rate.
Figure 3:
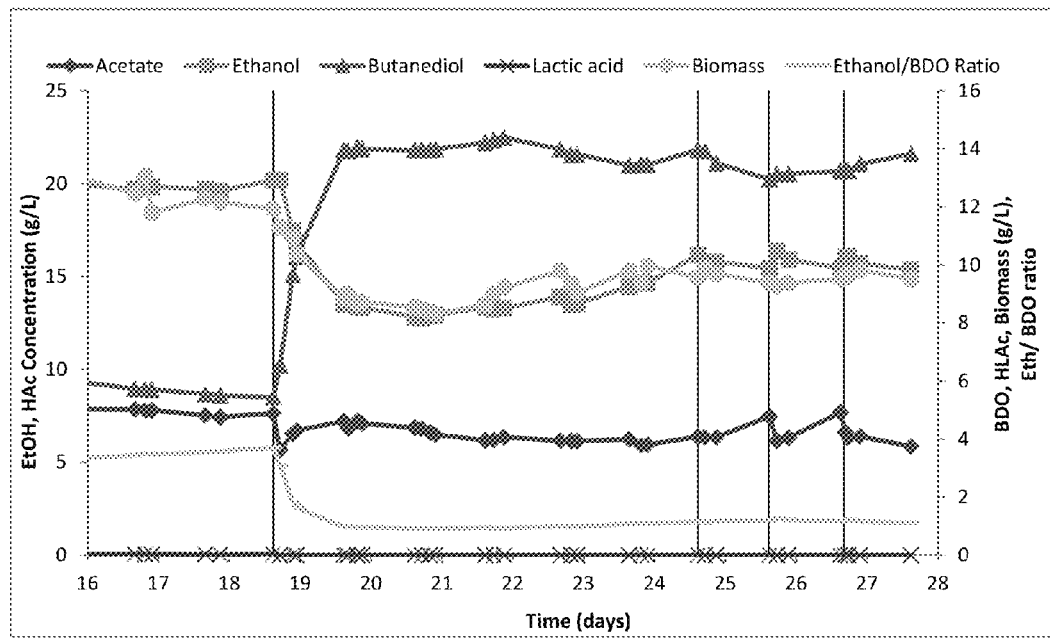
FIG. 3 shows the metabolite profile of a bioreactor where 2-HIBA was continuously added to the fermentation such that the concentration of 2-HIBA was maintained at 0.5 g/L (4.8 mM).

The 2,3-BDO concentration increased from 6 g/L to 12 g/L dropping the ratio from 4:1 to as low as 1.4:1. This addition was shown not to have a detrimental impact on gas uptake although ethanol and biomass concentration decreased as a result of the addition. The concentration of 2-HIBA was monitored in the reactor liquid outflow. The results of this are shown in FIG. 2. The curve indicates that this initial washout occurred at a rate similar to the dilution rate 1.8 day$^{-1}$ whilst the overall washout of 2-HIBA matched the bacterial dilution rate 0.7 day$^{-1}$. The results show that 2-HIBA is not converted in the reactor. The 2-HIBA washes out of the fermenter according to the bacterial dilution rate. This is important as it shows that the 2-HIBA is not consumed by the bacteria.

Example 2

A two reactor system was used to examine the impact of continuous 2-HIBA addition on the metabolite profile. Initially 0.5 g/L/day (4.8 mM/day) 2-HIBA was added to the R$_2$ only, this increased the production of 2,3-BDO but the ratio only dropped to as low as 1.9:1. Continuous addition of 2-HIBA at 0.5 g/L/day (4.8 mM/day) was then added to the R1. Because the 2-HIBA is not converted by the bacteria it was hypothesised that addition to the R1 would significantly increase the overall production of 2,3-BDO. This would be achieved by improving the concentration in both the R1 and the R2 as the 2-HIBA is transferred from the R1 to the R2 (through liquid flow) along with improved 2,3-BDO concentrations. The results from this continuous addition are shown in FIGS. 3-6. The 2,3-BDO concentration increased from 5.7 g/L to 14 g/L in the R1 and from 16 g/L to 21 g/L in the R$_2$ (see FIGS. 3 and 4). The ratio of ethanol:2,3-BDO dropped to 1:1 in the R1 and 1.3:1 in the R2 and remained stable for a period of eight days. The improvement of the ratio was achieved as a result of increased 2,3-BDO concentration and a drop in ethanol production.

Over time the ethanol concentration after the 2-HIBA addition improved whilst the concentration of 2,3-BDO remained stable, this had the effect of improving the total alcohol productivity of the system. As shown in the gas data (FIGS. 5 and 6) the addition of 2-HIBA did not negatively impact on the CO and hydrogen uptake. All parameters are summarised in Table 1 and 2. Table 2 shows the Metabolite averages for R1 and R2 in a linked two fermenter system across eight days of stable operation. Table 3 shows Gas data averages for R1 and R2 in a linked two fermenter system across eight days of stable operation. The Fermentation system lost stability due to a mechanical failure in the R1 control unit which resulted in agitation, temperature and pH control system failure and the collapse of the fermentation.

TABLE 2

| Average | Acetate g/L | Ethanol g/L | 2,3 BDO g/L | Lactate g/L | Biomass g/L | Ethanol:2,3 BDO | 2,3 BDO productivity g/L/day |
|---|---|---|---|---|---|---|---|
| R1 | 6.5 | 14.4 | 13.7 | 0.0 | 9.2 | 1.05:1 | 27 |
| R2 | 7.8 | 28.3 | 21.3 | 0.0 | 15.6 | 1.3:1 | 16 |

TABLE 3

| Average | CO uptake mMol/L | H2 production mMol/L | CO2 production mMol/L | CO utilisation % |
|---|---|---|---|---|
| R1 | −8830 | 423 | 5630 | 53 |
| R2 | −7930 | 413 | 4932 | 63 |

Example 3

Figure 7:
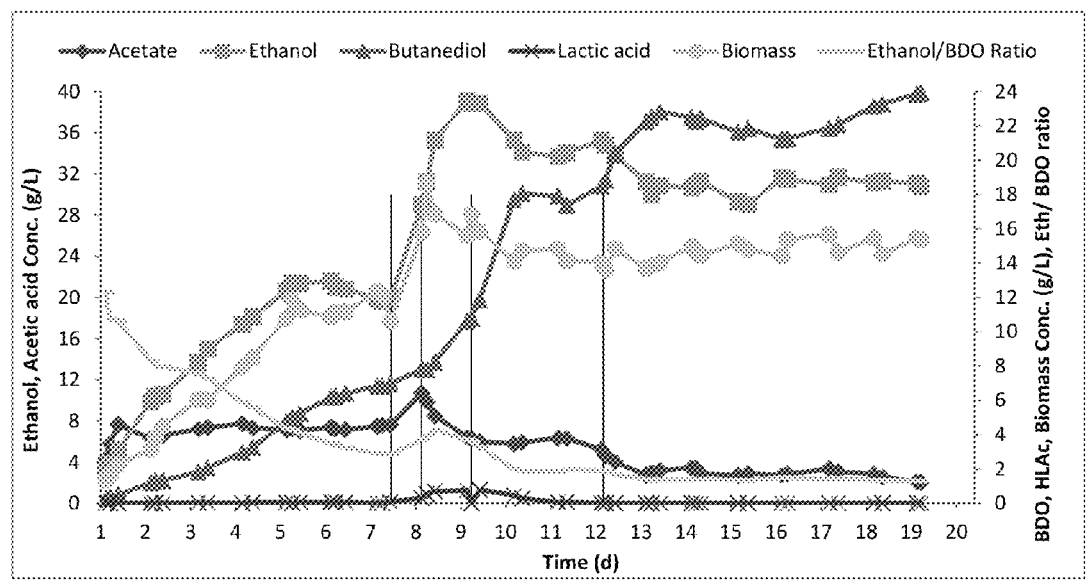
FIG. 7 shows the metabolite profile from a 2 reactor system where 2-HIBA concentration is increased from 0.5 g/L (4.8 mM) to 1.0 g/L (9.6 mM)

The results achieved in Example 2 were repeated with the aim to improve the overall titre of 2,3-BDO. In this experiment the 2-HIBA concentration was increased to 1 g/L/day (9.6 mM/day). As with the results achieved in the previous experiment the gas uptake was not negatively impacted and the ethanol:2,3-BDO ratio in the $R_2$ remained stable for a period of seven days at 1.3:1. The 1 g/L/day (9.6 mM/day) addition resulted in an improvement in the overall 2,3-BDO concentration which reached as high as 23.9 g/L (see FIG. 7).

Example 4

Determining the Minimum Concentration Needed to Illicit an Impact on 2,3-Butanedio Production In examples 1 to 3, concentrations of 0.5 g/L-1 g/L (4.8-9.6 mM) were tested and shown to significantly impact on the production of 2,3-butanediol and ethanol. In order to understand the minimum concentrations needed to generate the same effect the concentration used was dropped to 0.1 g/L (0.96 mM) in one example and 0.05 g/L (0.48 mM) in another example. Both fermentations had gas increased to minimize acetate and maximize ethanol production. Additional $CO_2$ was blended into the gas stream to maximize 2,3-BDO production, the gas blend used was 50% CO, 35% $CO_2$, 1.5% $H_2$ with $N_2$ balance. The dilution rate and bacterial dilution rate were adjusted to 1.8 day$^{-1}$ and 0.8 day$^{-1}$ respectively. Once stable data was collected continuous 2-HIBA addition through the media was started and resulting impact on metabolite concentrations observed. A summary of data before and after addition for each example is presented in Table 4. In both examples the ratio before the addition of 2-HIBA was about 2:1, and the resulting impact on the Ethanol:2,3-BDO ratio was proportional to the concentration of 2-HIBA used. In the first example where 0.1 g/L (0.96 mM) was used the ratio improved to 1:1 and when the concentration was halved (in the second example) the response was an improvement in the ratio to only 1.5:1.

TABLE 4

Impact of different 2-HiBA concentrations on two different fermentations.

| Time (day) | Ethanol:BDO ratio | 2,3-BDO (g/L) | Ethanol (g/L) | CO uptake (mol/L/day) | Biomass (g/L) |
|---|---|---|---|---|---|
| Expt 1: Before HIBA addition | 2.1:1 | 9.67 | 20.33 | 9.4 | 10.7 |
| Expt 1: 0.96 mM/day HIBA addition | 1:1 | 16.35 | 17.05 | 9.8 | 9.83 |
| Expt 2: Before HIBA addition | 2.2:1 | 8.42 | 18.73 | 8.2 | 12.69 |
| Expt 2:0.48 mM/day HIBA addition | 1.5:1 | 10.56 | 15.56 | 8 | 12.14 |

Figure 8:
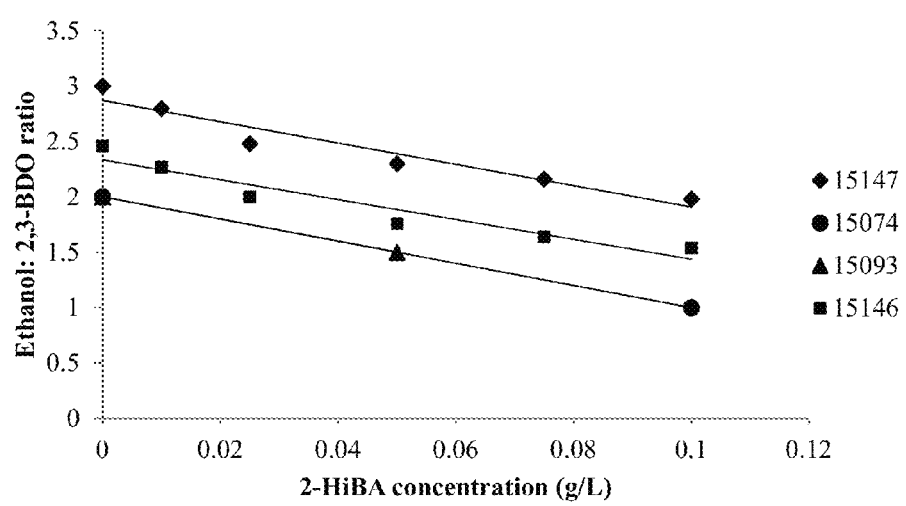
FIG. 8: shows the impact of different 2-HiBA concentrations on the Ethanol:2,3-BDO ratio.

In two further experiments concentrations from 0.01 g/L to 0.1 g/L (0.096, 0.24, 0.48, 0.72, 0.96 mM) were added and the impact on the metabolites observed. Again the fermentations had gas increased to minimize acetate and maximize ethanol production with $CO_2$ blended into the gas stream to maximize 2,3-BDO production. The dilution rate and bacterial dilution rate were adjusted to 1.8 day$^{-1}$ and 0.9 day$^{-1}$ respectively. The gas blend used was 42% CO, 35% $CO_2$, 1.5% $H_2$ with N2 balance. Collating the data, from all four examples, shows that for every 0.05 g/L (0.48 mM) added to a stable fermentation the Ethanol:2,3-BDO ratio drops by 0.5 units. These results are shown in FIG. 8. These results show the impact of 2-HiBA is independent of the starting ethanol:2,3-butanediol ratio, it also shows that concentrations as low as 0.01 g/L (0.096 mM) impacts on the production of 2,3-butanediol.

Example 5

Figure 9:
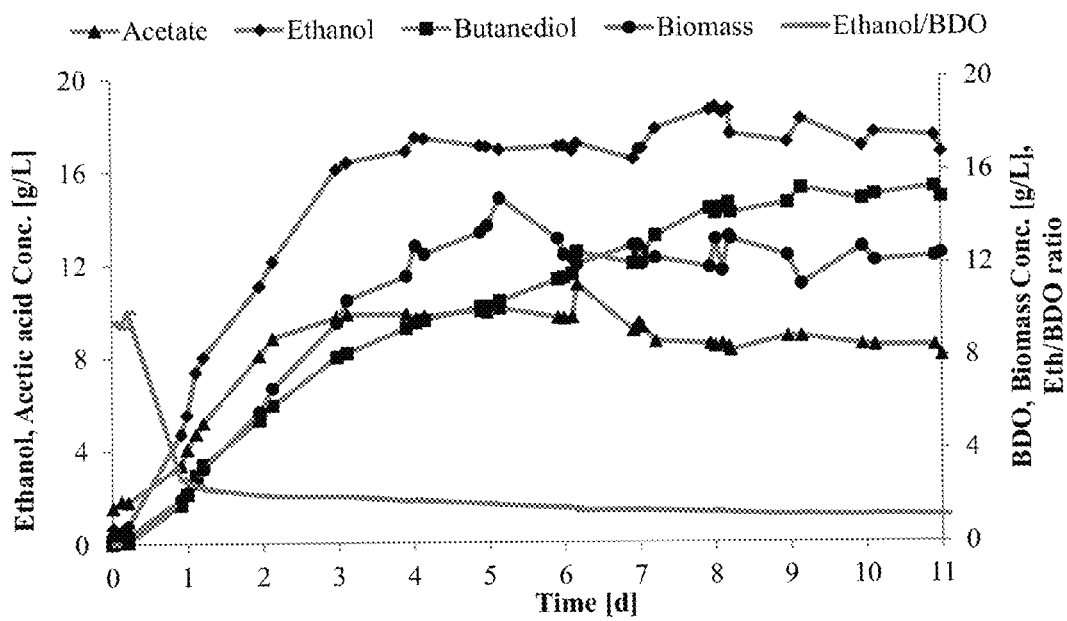
FIG. 9: shows the metabolite profile of fermentation with 0.05 g/L (0.48 mM) 2-HIBA in the media.
Figure 10:
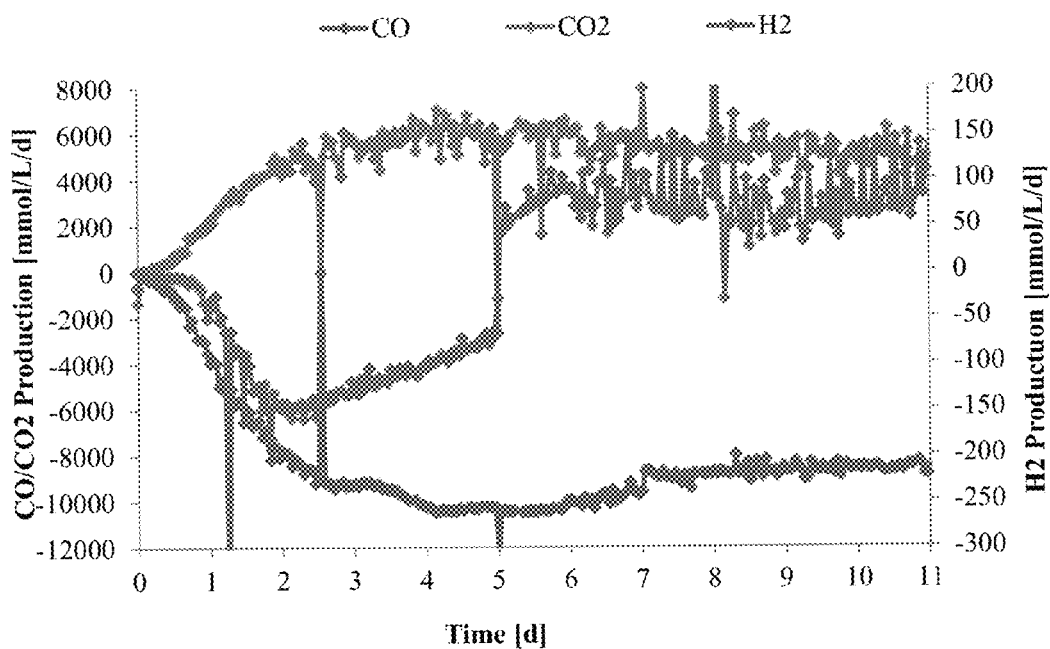
FIG. 10: shows the gas profile of fermentation with 0.05 g/L (0.48 mM) 2-HiBA in the media

To see if the 2-HIBA impacts negatively on growth a fermentation was started in the presence of 0.05 g/L (0.48 mM) 2-HIBA. During growth gas and agitation were increased so that by day 5.0 the agitation had reached a maximum of 950 rpm and the gas flow 800 ml/min. At this time the dilution rate was 1.8 day$^{-1}$ and the bacterial dilution rate 0.85 day$^{-1}$. The presence of 2-HIBA had no impact on the growth of the fermentation but did increase how quickly a low Ethanol:2,3-Butanediol ratio could be achieved. By day 2.0 the Ethanol:2,3-BDO ratio had reached 2:1 and then continued to slowly drop, with the ratio eventually reaching 1.1:1 with an average ethanol concentration of 17 g/L and 2,3-butanediol concentration of 15.5 g/L. Results for this fermentation are shown in FIG. 9 and FIG. 10. These results show that is possible to add 2-HiBA in the fermentation media without a negative impact on growth with 0.05 g/L (0.48 mM) sufficient to achieve an Ethanol:2,3-BDO ratio in the range of 1:1.

Example 6

_2-HIBA Gene Expression

In order to understand the impact of 2-HIBA on the metabolism of LZ1561 samples were taken for gene expression analysis. A reactor was started up as a batch and after 1 day was turned continuous at a D=1.4 day$^{-1}$. Gas flow and agitation were adjusted in order to minimise acetate and maximise ethanol and 2,3-BDO production. By day 7 the Ethanol:2,3-BDO ratio was less than 5:1 and the gas had reached target CO uptake of between 5-6 mol/L/day. On day 9.6 a sample was taken for gene expression analysis representing stable data without 2-HIBA. On day 10.78 0.5 g/L (4.8 mM_ 2-HIBA was added to the fermentation as an injection and then through addition in the media bottle. Following the addition of 2-HIBA a characteristic response in metabolites was seen, this included decreasing acetate, ethanol and biomass with increasing 2,3-BDO. On day 13.8 another gene expression sample was taken representing stable 2-HIBA addition. Table 5 indicates the two time points where data was collected for gene expression analysis. Before the addition of 2-HIBA the Ethanol:2,3-BDO ratio was 4:1, after addition the ratio reached 1.5:1. A small subset of genes were found to be significantly up-regulated or down-regulated these genes are shown in Table 6 and Table 7. The results for this analysis indicated very clearly that 2-HIBA interacts with the Branch Chain Amino Acid biosynthesis pathway (BCAA). From the results a mode of action of 2-HIBA was proposed and this is illustrated and described in FIG. 11.

TABLE 5

Samples taken for differential gene expression analysis

| Time (day) | Ethanol:BDO ratio | Operational notes | Samples taken | Dilution rate (day$^{-1}$) | CO uptake (mol/L/day) | Biomass (g/L) |
|---|---|---|---|---|---|---|
| 1. Day 8.6-10.6 | 4:1 | Steady state | RNA in duplicate | 1.41 | 5.7 | 4.7 |
| 2. Day 12.8-14.0 | 1.5:1 | Stable 0.5 g/L HIBA addition | RNA in duplicate | 1.37 | 5.1 | 3.45 |

TABLE 6

Figure 4:
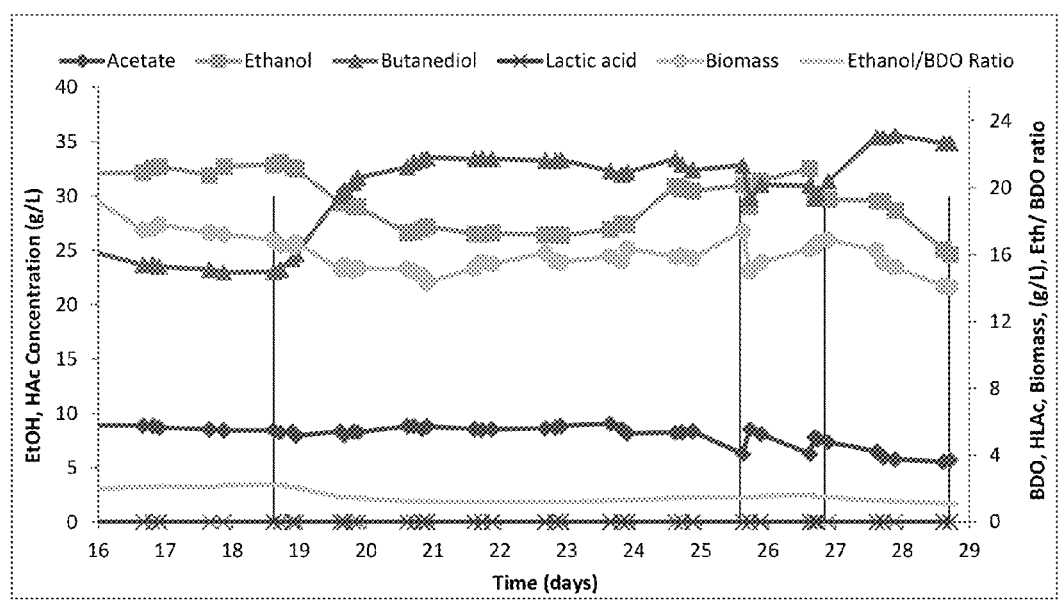
FIG. 4 shows the metabolite profile of a bioreactor wherein the amount of 2-HIBA continuously added to the fermentation was increased to 1.0 g/L (9.6 mM).
Figure 5:
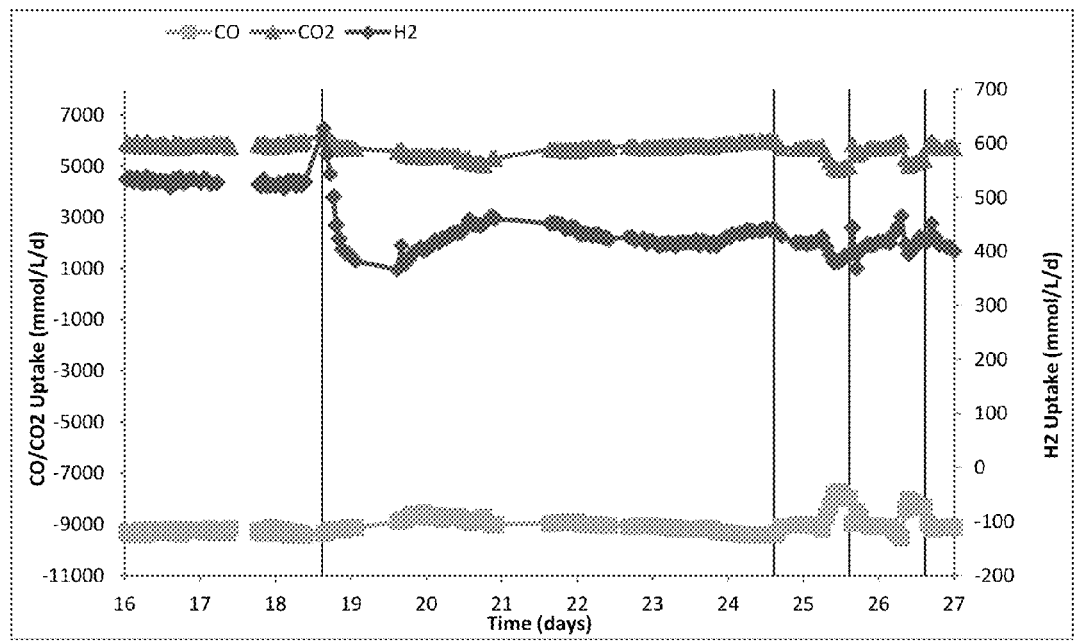
FIG. 5 shows the gas profile of a bioreactor, where 2-HIBA was continuously added to the fermentation such that the concentration of 2-HIBA was maintained at 0.5 g/L (4.8 mM).
Figure 6:
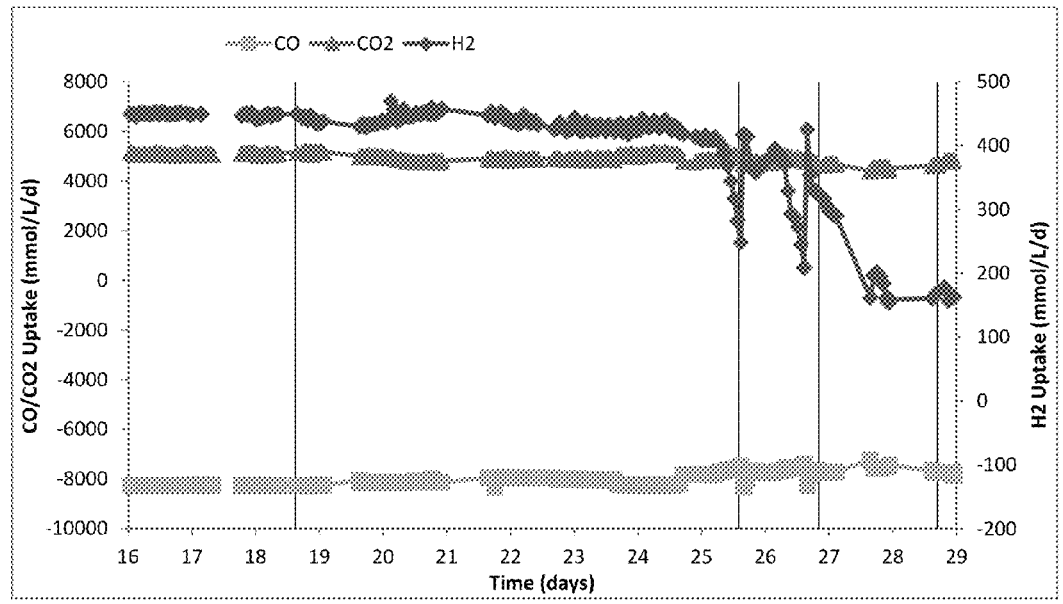
FIG. 6 shows the gas profile of a bioreactor, where the amount of 2-HIBA continuously added to the fermentation was increased to 1.0 g/L (9.6 mM).

Differentially up-regulated genes between 0 mM 2-HIBA addition and 4.8 mM 2-HIBA addition, these enzymes are visualised in FIG. 4.

| Pathway position | ORF | Annotation | log2 fold_change | p_value | q_value |
|---|---|---|---|---|---|
| 1 | or2389 | acetolactate synthase, large subunit, biosynthetic type CDS | 3.25457 | 0.0001 | 0.0019 |
| 1 | or2390 | acetolactate synthase, small subunit CDS | 3.23743 | 5e−05 | 0.0010 |
| 2 | or2387 | Ketol-acid reductoisomerase CDS | 3.20184 | 5e−05 | 0.0010 |
| 3 | or2388 | Dihydroxy-acid dehydratase CDS | 2.90072 | 5e−05 | 0.0010 |
| 4 | or1190 | 2-isopropylmalate synthase CDS | 3.62992 | 5e−05 | 0.0010 |
| 5 | or1191 | 3-isopropylmalate dehydratase large subunit CDS | 3.54966 | 5e−05 | 0.0010 |
| 6 | or1193 | 3-isopropylmalate dehydrogenase CDS | 3.28912 | 0.0011 | 0.0151 |
|  | or2461 | General substrate transporter CDS | 2.86681 | 5e−05 | 0.0010 |

Example 7

TABLE 7

Differentially down-regulated genes between 0 mM 2-HIBA addition and 4.8 mM 2-HIBA addition

| Pathway position | ORF | Annotation | log2 fold_change | p_value | q_value |
|---|---|---|---|---|---|
| | or1907 | Indole-3-glycerol phosphate synthase CDS | −3.04226 | 5e−05 | 0.0010 |
| | or3076 | hypothetical protein CDS | −3.46918 | 5e−05 | 0.0010 |
| | or2161 | Alcohol dehydrogenase CDS | −3.47608 | 5e−05 | 0.0010 |
| | or2739 | Glutamate synthase (NADPH) CDS | −3.49801 | 5e−05 | 0.0010 |
| | or3080 | transcriptional regulator, CdaR CDS | −3.94661 | 5e−05 | 0.0010 |
| | or3079 | Methylglyoxal reductase (NADPH-dependent) CDS | −4.01988 | 5e−05 | 0.0010 |
| | or3075 | Glucarate dehydratase CDS | −4.08444 | 5e−05 | 0.0010 |
| | or2997 | Glycerol dehydrogenase CDS | −4.92397 | 5e−05 | 0.0010 |

Monitoring BCAA Production During 2-HIBA Addition

Figure 11:
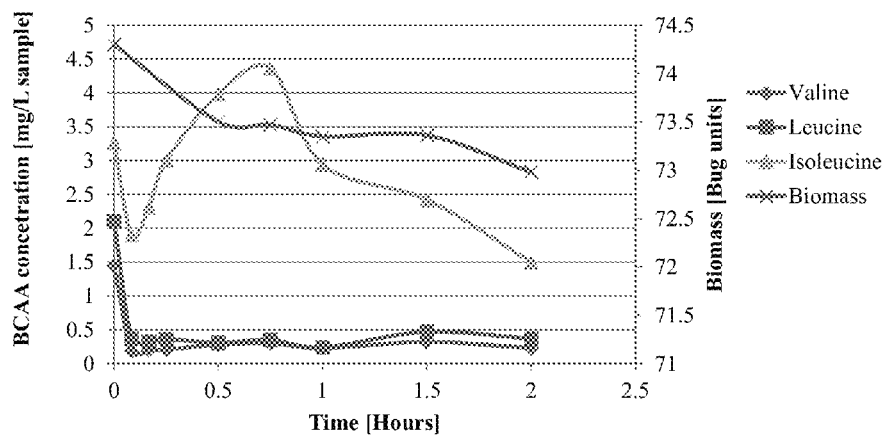
FIG. 11: shows the branch chain amino acid and biomass concentration following 100 mg (0.96 mM) HiBA addition

In order to generate further evidence that 2-HiBA interferes with branch chain amino acid production, the concentrations of these amino acids were monitored directly before and after the addition of 2-HIBA. FIG. 11 illustrates the results; immediately after the addition of 2-HIBA the concentrations of valine, leucine and isoleucine drop as well as biomass. Over time the biomass concentration flattens out and the concentration of isoleucine appears to recover with the concentration of leucine and valine remaining lower than the value before 2-HIBA addition. This data appears to collaborate the gene expression data that shows that 2,3-BDO production increases due to an interference of the branch chain amino acid pathway.

Addition of Other Known Inhibitors 2-hydroxy-2-methylbutyrate was added to a fermentation optimized for 2,3-Butanediol production. This chemical was chosen based on its structural relatedness to 2-HiBA and its reference in the literature as a known inhibitor of ilvC. A single addition of 2-hydroxy-2-methylbutyric acid (15 mM) was added to a stable reactor on day 13.2 and the results on the metabolite profile observed. The results are shown in FIG. 13. The addition appeared to increase the production of 2,3-Butanediol and drop the Ethanol:2,3-BDO ratio.

Example 8

Reduced Flux from Acetolactate to 2,3-Dihydroxy-3-Methylbutyrate

To inhibit flux from acetolactate to 2,3-dihydroxy-3-methylbutyrate a ketol-acid reductoisomerase gene is eliminated. This can be achieved by gene disruption using the ClosTron System (Heap et al 2007).

The knockout of the ketol-acid reductoisomerase gene requires that the fermentation is operated in the presence of supplemental branched-chain amino acids, since it is a required gene for biosynthesis of branched-chain amino acids, which are essential for microbial growth. The branched-chain amino acids are added at limiting levels, such that the pathway for branched-chain amino acid biosynthesis is up regulated and active.

Alternatively, the native ketol-acid reductoisomerase gene (SEQ ID No: 1) is eliminated by the mechanism described above, and an exogenous ketol-acid reductoisomerase gene which has a lower activity than the native gene is inserted into the microorganism. The exogenous ketol-acid reductoisomerase gene can be either a homologous enzyme from another organism which has lower activity in the host, or a mutant of the native enzyme which has lowered activity. Mutations to the active site which reduce the activity have been identified in *Escherichia coli* (Tyagi et al 2005), and key residues are conserved in *C. autoethanogenum*, allowing these mutations to be replicated to generate a mutant of the native enzyme with reduced activity. The elimination of the native gene and replacement with a less active gene results in a strain which has reduced flux from acetolactate toward branched-chain amino acids. The pool of acetolactate available is increased as a consequence.

Example 9

Increased Flux from Pyruvate to 2-hydroxy-2-methyl-3-ketobutyrate (acetolactate)

To increase flux from pyruvate to 2-hydroxy-2-methyl-3-ketobutyrate (acetolactate) the native catabolic acetolactate synthase is overexpressed.

The native catabolic acetolactate synthase gene (alsS) (SEQ ID No: 2) is cloned into the NdeI and NheI sites of pMTL83155 (WO2013185123A1) to generate an overexpression plasmid, expressing alsS under the control of the promoter region of the phosphotransacetylase-acetate kinase operon.

The overexpression plasmid can be similarly produced using a catabolic acetolactate synthase from another microorganism, a native anabolic acetolactate synthase, or an anabolic acetolactate synthase from another microorganism.

It is considered that the use of either a catabolic acetolactate synthase from another microorganism or an anabolic acetolactate synthase from another microorganism can have a higher affinity toward pyruvate and faster reaction kinetics. It is further considered that the anabolic acetolactate synthase from another microorganism can be an enzyme which is identified to be insensitive to feedback inhibition. It is also considered that the small subunit of the anabolic acetolactate synthase mutant which is insensitive to feedback inhibitions is overexpressed.

The overexpression plasmid is introduced into *Clostridium autoethanogenum*. This result in a *C. autoethanogenum* strain adapted to increase flux from pyruvate to acetolactate.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, headings, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

We claim:

1. A method of increasing the production of at least one fermentation product, said method comprising:
   a. providing a gaseous substrate comprising CO to a bioreactor comprising a culture of at least one acetogenic carboxydotrophic microorganism in a liquid nutrient medium,
   b. fermenting said culture of at least one acetogenic carboxydotrophic microorganism to produce at least one fermentation product from said gaseous substrate; and
   c. inhibiting flux of carbon to branched chain amino acids by adding at least one compound to said liquid nutrient medium, wherein said at least one compound is selected from the group consisting of 2-hydroxybutyric acid (2-HIBA), 2-hydroxyl-2-methylbutyric acid, 2-hydroxybutyrate, 2-hydroxy-3-methylbutyric acid, 2-keto-3-hydroxyisovalerate and 2-ketoisovalerate, thereby increasing said production of at least one fermentation product.

2. The method of claim 1, wherein said at least one fermentation product is selected from the group consisting of acetic acid, ethanol, 2,3-butanediol, 2-butanone, 2-butanol, acetoin, iso-propanol, lactate, succinate, methyl ethyl ketone (MEK), propanediol, 2-propanol, iso-butanol, citramalate, butadiene, poly lactic acid, 3-hydroxybutyrate, isobutylene, 3-hydroxy propionate (3HP), acetone and fatty acids.

3. The method of claim 1, wherein said at least one fermentation product is selected from the group consisting of 2,3-butanediol, 2-butanone, 2-butanol and acetoin.

4. The method of claim 1, wherein said gaseous substrate further comprises $H_2$ and $CO_2$.

5. The method of claim 1, wherein said at least one acetogenic carboxydotrophic microorganism is selected from the group consisting of *Clostridium, Moorella, Oxobacter, Peptostreptococcus, Acetobacterium, Eubacterium* or *Butyribacterium*.

6. The method of claim 5, wherein said at least one acetogenic carboxydotrophic microorganism is selected from the group consisting of *Clostridium autoethanogenum, Clostridium ljungdahli, Clostridium carboxidivorans, Clostridium drakei, Clostridium scatologenes, Clostridium aceticum, Clostridium formicoaceticum, Clostridium magnum, Butyribacterium methylotrphoicum, Acetobacterium woodii, Alkalibaculum bacchi, Blautia producta, Eubacterium limosum, Moorella thermoacetica, Sporomusa ovata, Sporomusa silvacetica, Sporomusa sphaeroides, Oxobacter pfennigii* and *Thermoanaerobacter kiuvi*.

7. A method of increasing the production of 2,3-butanediol, the method comprising;
 a. providing a gaseous substrate comprising CO to a bioreactor comprising a culture of at least one acetogenic carboxydotrophic microorganism in a liquid nutrient medium,
 b. fermenting said culture of at least one acetogenic carboxydotrophic microorganism to produce at least 2,3-butanediol from said gaseous substrate; and
 c. inhibiting flux of carbon to branched chain amino acids by adding at least one compound to said liquid nutrient medium, wherein said at least one compound is selected from the group consisting of 2-hydroxybutyric acid (2-HIBA), 2-hydroxyl-2-methylbutyric acid, 2-hydroxybutyrate, 2-hydroxy-3-methylbutyric acid, 2-keto-3-hydroxyisovalerate and 2-ketoisovalerate, thereby increasing said production of 2,3-butanediol.

8. The method of claim 7, wherein said fermenting of step b further produces at least one product selected from the group consisting of acetic acid, ethanol, 2 butanone, 2-butanol, acetoin, isopropanol, lactate, succinate, methyl ethyl ketone (MEK), propanediol, 2-propanol, iso-butanol, citramalate, butadiene, poly lactic acid, 3-hydroxybutyrate, isobutylene, 3-hydroxy propionate (3HP), acetone and fatty acids.

9. The method of claim 7 wherein said at least one compound is 2-HIBA.

10. The method of claim 7, wherein said at least one acetogenic carboxydotrophic microorganism is selected from the group consisting of *Clostridium, Moorella, Oxobacter, Peptostreptococcus, Acetobacterium, Eubacterium* or *Butyribacterium*.

11. The method of claim 7, wherein said 2,3-butanediol is produced at a rate of at least 10 g/L per day.

12. The method of claim 7, wherein said fermenting of step b further produces ethanol, at a ratio of ethanol to 2,3-butanediol i-s between 4:1 and 1:2.

13. A method of increasing the production of at least one product derived from acetolactate, said method comprising:
 a. providing a gaseous substrate comprising CO to a bioreactor comprising a culture of at least one recombinant acetogenic carboxydotrophic microorganism in a liquid nutrient medium,
 b. fermenting said culture of at least one recombinant acetogenic carboxydotrophic microorganism to produce at least one fermentation product from said gaseous substrate;
 wherein said at least one recombinant acetogenic carboxydotrophic microorganism comprises a genetic modification to increase conversion of pyruvate to acetolactate, wherein said genetic modification comprises overexpression of an acetolactate synthase gene in said recombinant acetogenic carboxydotrophic microorganism in comparison to a parental acetogenic carboxydotrophic microorganism without said overexpression and a mutation in a gene encoding a ketol-acid reductoisomerase enzyme that reduces the activity of said ketol-acid reductoisomerase enzyme in said recombinant acetogenic carboxydotrophic microorganism in comparison to a parental acetogenic carboxydotrophic microorganism without said mutation, thereby increasing said production of at least one product derived from acetolactate.

* * * * *